(12) United States Patent
Gonzales et al.

(10) Patent No.: US 9,540,593 B2
(45) Date of Patent: *Jan. 10, 2017

(54) LIQUID CLEANING AND/OR CLEANSING COMPOSITION

(71) Applicant: The Procter & Gamble Company, Cincinnati, OH (US)

(72) Inventors: Denis Alfred Gonzales, Brussels (BE); Michael Leslie Groombridge, Newcastle upon Tyne (GB); Michael McDonnell, Northumberland (GB); Gregor Anton Meissner, Hanau (DE); Dominic Michael Piff, Little Sandhurst (GB)

(73) Assignee: The Procter & Gamble Company, Cincinnati, OH (US)

( * ) Notice: Subject to any disclaimer, the term of this patent is extended or adjusted under 35 U.S.C. 154(b) by 85 days.

This patent is subject to a terminal disclaimer.

(21) Appl. No.: 14/315,350

(22) Filed: Jun. 26, 2014

(65) Prior Publication Data

US 2015/0007399 A1  Jan. 8, 2015

(30) Foreign Application Priority Data

Jul. 2, 2013  (EP) .................................... 13174496

(51) Int. Cl.
*C11D 3/14* (2006.01)
*C11D 3/37* (2006.01)
(Continued)

(52) U.S. Cl.
CPC ................ *C11D 3/14* (2013.01); *A61K 8/0208* (2013.01); *A61K 8/0245* (2013.01); *A61K 8/25* (2013.01);
(Continued)

(58) Field of Classification Search
None
See application file for complete search history.

(56) References Cited

U.S. PATENT DOCUMENTS 3,183,071 A  5/1965  Rue et al.
9,163,201 B2 * 10/2015  Gonzales ........... C11D 17/0013
(Continued)

FOREIGN PATENT DOCUMENTS

EP  2338963 A1  6/2011
GB  1418671  * 12/1975
(Continued)

OTHER PUBLICATIONS

Thomson Scientific, Londob. GB; Yunichika KK; XP002721819, Mar. 26, 2013; 2 Pages.
(Continued)

*Primary Examiner* — Lorna Douyon
(74) *Attorney, Agent, or Firm* — Lauren Christine Gonzalez; Gary J. Foose; John Todd Dipre

(57) ABSTRACT

A liquid cleaning and/or cleansing composition comprising non-spherical and/or non-rolling abrasive cleaning particles wherein the abrasive cleaning particles comprise extruded, and/or three-dimensional printed, elements having a longitudinal length "L" extending parallel to a z-axis and a complex cross-sectional shape extending on a plane perpendicular to the longitudinal length "L" and parallel to an x-y plane, wherein the complex cross-sectional shape comprises one or more elongate protrusions projecting in a direction parallel to the longitudinal length "L", each protrusion having at least one edge, and wherein the complex cross-sectional shape is a predetermined non-random cross-sectional shape.

19 Claims, 2 Drawing Sheets

(51) Int. Cl.
  *C11D 17/00*  (2006.01)
  *C11D 17/04*  (2006.01)
  *A61K 8/02*  (2006.01)
  *B29C 47/00*  (2006.01)
  *A61K 8/25*  (2006.01)
  *A61K 8/26*  (2006.01)
  *A61Q 5/02*  (2006.01)
  *A61Q 11/00*  (2006.01)
  *A61K 8/73*  (2006.01)
  *A61K 8/85*  (2006.01)
  *A61Q 19/10*  (2006.01)
  *A61K 8/97*  (2006.01)

(52) U.S. Cl.
  CPC ............. *A61K 8/26* (2013.01); *A61K 8/731* (2013.01); *A61K 8/85* (2013.01); *A61K 8/97* (2013.01); *A61Q 5/02* (2013.01); *A61Q 11/00* (2013.01); *A61Q 19/10* (2013.01); *B29C 47/0004* (2013.01); *C11D 3/37* (2013.01); *C11D 17/0013* (2013.01); *C11D 17/049* (2013.01); *A61K 2800/28* (2013.01)

(56) References Cited

U.S. PATENT DOCUMENTS

| | | | |
|---|---|---|---|
| 2011/0150949 A1 | 6/2011 | Gonzales et al. | |
| 2011/0150950 A1* | 6/2011 | Gonzales | A61K 8/025 424/401 |
| 2011/0150951 A1* | 6/2011 | Gonzales | A61K 8/025 424/401 |
| 2011/0262371 A1 | 10/2011 | Deleersnyder et al. | |
| 2011/0262504 A1* | 10/2011 | Deleersnyder | A61K 8/0208 424/401 |
| 2012/0168979 A1 | 7/2012 | Bauer et al. | |
| 2012/0322713 A1* | 12/2012 | Perez-Prat Vinuesa | C11D 3/2072 510/236 |
| 2013/0039961 A1* | 2/2013 | Gonzales | A61K 8/8117 424/401 |
| 2014/0352722 A1* | 12/2014 | Gonzales | C11D 17/0013 134/7 |

FOREIGN PATENT DOCUMENTS

WO  WO 02/090483 A2  11/2002
WO  WO 2013/106597 A1  7/2013

OTHER PUBLICATIONS

PCT Search Report: Dated Sep. 19, 2014; PCT/US2014/044017; 10 Pages.
U.S. Appl. No. 14/315,353, filed Jun. 26, 2014, Gonzales, et al.

* cited by examiner

LIQUID CLEANING AND/OR CLEANSING COMPOSITION

TECHNICAL FIELD

The present invention relates to liquid compositions for cleaning and/or cleansing a variety of inanimate and animate surfaces, including hard surfaces in and around the house, dish surfaces, hard and soft tissue surface of the oral cavity, such as teeth, gums, tongue and buccal surfaces, human and animal skin or hair, car and vehicles surfaces, etc. More specifically, the present invention relates to liquid scouring compositions comprising suitable particles for cleaning and/or cleansing. Most preferably the present invention relates to a hard surface composition for treating inanimate hard surfaces.

BACKGROUND OF THE INVENTION

Scouring compositions such as particulate compositions or liquid (incl. gel, paste-type) compositions containing abrasive components are well known in the art. Such compositions are used for cleaning and/or cleansing a variety of surfaces; especially those surfaces that tend to become soiled with difficult to remove stains and soils.

Amongst the currently known scouring compositions, the most popular ones are based on abrasive particles with shapes varying from spherical to irregular. The most common abrasive particles are either inorganic like carbonate salt, clay, silica, silicate, shale ash, perlite and quartz sand or organic polymeric beads like polypropylene, PVC, melamine, urea, polyacrylate and derivatives, and come in the form of liquid composition having a creamy consistency with the abrasive particles suspended therein.

The surface safety profile of such currently known scouring compositions is inadequate alternatively, poor cleaning performances is shown for compositions with an adequate surface safety profile. Indeed, due to the presence of very hard abrasive particles, these compositions can damage, i.e., scratch, the surfaces onto which they have been applied.

To address some of these problems, shaped abrasive particles such as those described in EP 2 338 966 A1 have been developed in order to provide effective cleaning and surface safety.

However, there still remains a need to improve the cleaning abilities of abrasive particles as well as simplifying the processability necessary to ensure consistent and appropriate particle shape as well as strength.

It is an advantage of the compositions according to the present invention that they may be used to clean/cleanse inanimate and animate surfaces made of a variety of materials like glazed and non-glazed ceramic tiles, enamel, stainless steel, Inox®, Formica®, vinyl, no-wax vinyl, linoleum, melamine, glass, plastics, painted surfaces, human and animal skin, hair, hard and soft tissue surface of the oral cavity, such as teeth enamel, gums, tongue and buccal surfaces, and the like.

A further advantage of the present invention is that in the compositions herein, the particles can be formulated at very low levels, whilst still providing the above benefits.

SUMMARY OF THE INVENTION

The present invention is directed to a liquid cleaning and/or cleansing composition comprising non-spherical and/or non-rolling abrasive cleaning particles wherein the abrasive cleaning particles comprise extruded, and/or three-dimensional printed, elements having a longitudinal length "L" extending parallel to a z-axis and a complex cross-sectional shape extending on a plane perpendicular to the longitudinal length "L" and parallel to an x-y plane, wherein the complex cross-sectional shape comprises one or more elongate protrusions each having at least one edge, and wherein the complex cross-sectional shape is a predetermined non-random cross-sectional shape.

The present invention further encompasses a process generating shaped non-spherical and/or non-rolling abrasive cleaning particles for use in a liquid cleaning and/or cleansing composition.

The present invention further encompasses a kit comprising the liquid cleaning and/or cleansing composition and a substrate.

DETAILED DESCRIPTION OF THE INVENTION

Figure 1:
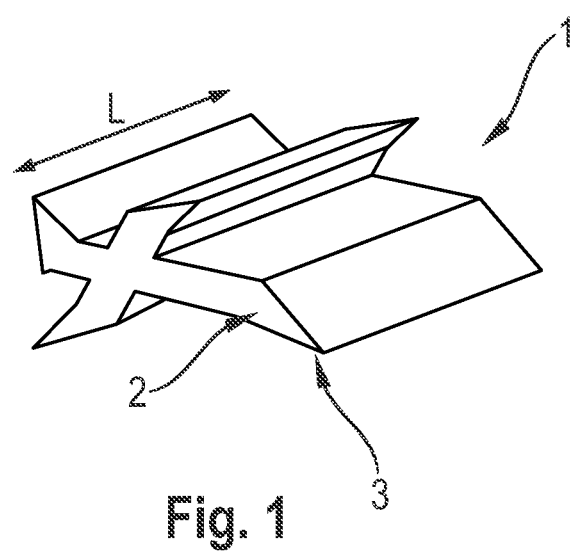
FIG. 1 is drawing showing an illustration of an exemplary particle of the present invention.

As used herein "abrasive particles" means abrasive cleaning particles comprising extruded, and/or three dimensionally "3D" printed, elements of a predetermined shape.

As used herein "substantially water-insoluble" means that the material referred to has a solubility of less than 30 g per 100 g of water, preferably less than 20 g per 100 g of water, more preferably less than 10 g per 100 g of water, more preferably less than 5 g per 100 g of water, even more preferably less than 2 g per 100 g of water, most preferably less than 1 g per 100 g of water, at room temperature (20° C.) and atmospheric pressure (101 kPa).

As used herein "complex cross-sectional shape" means that said cross-sectional shape is predetermined and preferably at least partly irregular such to define a non-symmetric perimeter about at least one axis parallel to an x-axis or a y-axis.

As used herein "z-axis" means an axis parallel to the length of the element and/or the extruding axis.

As used herein the "x-y plane" means a plane perpendicular to the z-axis and is typically parallel to a plane on which the perimeter of the complex cross-sectional shape lies.

As used herein "substantially the entire length "L"" means at least 70%, preferably at least 85%, preferably at least 90%, more preferably at least 95%, most preferably at least 98%, of length "L".

As used herein "substantially perpendicular" means from 45° to 90°, preferably from 50° to 90°, more preferably from 60° to 90°, even more preferably from 70° to 90°, most preferably from 80° to 90°, taken from an axis parallel to the cleaning direction.

As used herein "same shape" means at least 80%, preferably at least 85%, more preferably at least 90%, most preferably at least 95% identity, as determined by image analysis software such as available in the nano 500 from Occhio or G3 from Malvern shape analyzing instruments.

The Liquid Cleaning/Cleansing Composition

The compositions according to the present invention are designed as cleaners/cleansers for a variety of inanimate and animate surfaces. Preferably, the compositions herein are suitable for cleaning/cleansing surfaces selected from the group consisting of inanimate surfaces, animate surfaces, and combinations thereof.

In a preferred embodiment, the compositions herein are suitable for cleaning/cleansing inanimate surfaces selected from the group consisting of household hard surfaces; dish surfaces; surfaces like leather or synthetic leather; and automotive vehicle surfaces.

In a highly preferred embodiment, the compositions herein are suitable to clean household hard surfaces.

By "household hard surface", it is meant herein any kind of surface typically found in and around houses like kitchens, bathrooms, e.g., floors, walls, tiles, windows, cupboards, sinks, showers, shower plastified curtains, wash basins, WCs, fixtures and fittings and the like made of different materials like ceramic, vinyl, no-wax vinyl, linoleum, melamine, glass, Inox®, Formica®, any plastics, plastified wood, metal or any painted or varnished or sealed surface and the like. Household hard surfaces also include household appliances including, but not limited to refrigerators, freezers, washing machines, automatic dryers, ovens, microwave ovens, dishwashers and so on. Such hard surfaces may be found both in private households as well as in commercial, institutional and industrial environments.

By "dish surfaces" it is meant herein any kind of surfaces found in dish cleaning, such as dishes, cutlery, cutting boards, pans, and the like. Such dish surfaces may be found both in private households as well as in commercial, institutional and industrial environments.

In an another preferred embodiment, the compositions herein are suitable for cleaning/cleansing animate surfaces selected from the group consisting of human skin; animal skin; human hair; animal hair; and inter-dental areas such as teeth, gums and the like.

The compositions according to the present invention are liquid compositions as opposed to a solid or a gas. Liquid compositions include compositions having a water-like viscosity as well as thickened compositions, such as gels and pastes.

In a preferred embodiment herein, the liquid compositions herein are aqueous compositions. Therefore, they may comprise from 65% to 99.5% by weight of the total composition of water, preferably from 75% to 98% and more preferably from 80% to 95%.

In another preferred embodiment herein, the liquid compositions herein are mostly non-aqueous compositions although they may comprise from 0% to 10% by weight of the total composition of water, preferably from 0% to 5%, more preferably from 0% to 1% and most preferably 0% by weight of the total composition of water.

In a preferred embodiment herein, the compositions herein are neutral compositions, and thus have a pH, as is measured at 25° C., of 3 to 10, preferably 4 to 9, more preferably 5 to 8.

In other preferred embodiment compositions have pH above 4, preferably above 7, more preferably above 9, most preferably above 10.5 and alternatively have pH preferably from 2 to below 9, preferably from 2.5 to 7.5.

Accordingly, the compositions herein may comprise suitable bases and acids to adjust the pH.

A suitable base to be used herein is an organic and/or inorganic base. Suitable bases for use herein are the caustic alkalis, such as sodium hydroxide, potassium hydroxide and/or lithium hydroxide, and/or the alkali metal oxides such, as sodium and/or potassium oxide or mixtures thereof. A preferred base is a caustic alkali, more preferably sodium hydroxide and/or potassium hydroxide.

Other suitable bases include ammonia, ammonium carbonate, all available carbonate salts such as $K_2CO_3$, $Na_2CO_3$, $CaCO_3$, $MgCO_3$, etc., alkanolamines (as e.g. monoethanolamine), urea and urea derivatives, polyamine, etc.

Typical levels of such bases, when present, are of from 0.01% to 5.0% by weight of the total composition, preferably from 0.05% to 3.0% and more preferably from 0.1% to 0.6%.

The compositions herein may comprise an acid to trim its pH to the required level, despite the presence of an acid, if any, the compositions herein will maintain their preferably neutral pH as described herein above. A suitable acid for use herein is an organic and/or an inorganic acid. A preferred organic acid for use herein has a pKa of less than 6. A suitable organic acid is selected from the group consisting of citric acid, lactic acid, glycolic acid, succinic acid, glutaric acid and adipic acid and a mixture thereof. A mixture of said acids may be commercially available from BASF under the trade name Sokalan® DCS. A suitable inorganic acid is selected from the group consisting hydrochloric acid, sulphuric acid, phosphoric acid and a mixture thereof.

A typical level of such an acid, when present, is of from 0.01% to 5.0% by weight of the total composition, preferably from 0.04% to 3.0% and more preferably from 0.05% to 1.5%.

In a preferred embodiment, the composition according to the present invention contains citric acid, preferably alone or in combination with other acids, at a level of from greater than 0% to less than 0.5% by weight of the composition. It has surprisingly been found that citric acid at this level improves the cleaning effect of the abrasive particles.

In a preferred embodiment according to the present invention the compositions herein are thickened compositions. Preferably, the liquid compositions herein have a viscosity of up to 7500 cps at 20 $s^{-1}$, more preferably from 5000 cps to 50 cps, yet more preferably from 2000 cps to 50 cps and most preferably from 1500 cps to 300 cps at 20 $s^{-1}$ and 20° C. when measured with a Rheometer, model AR 1000 (Supplied by TA Instruments) with a 4 cm conic spindle in stainless steel, 2° angle (linear increment from 0.1 to 100 $sec^{-1}$ in max. 8 minutes).

In another preferred embodiment according to the present invention the compositions herein have a water-like viscosity. By "water-like viscosity" it is meant herein a viscosity that is close to that of water. Preferably the liquid compositions herein have a viscosity of up to 50 cps at 60 rpm, more preferably from 0 cps to 30 cps, yet more preferably from 0 cps to 20 cps and most preferably from 0 cps to 10 cps at 60 rpm and 20° C. when measured with a Brookfield digital viscometer model DV II, with spindle 2.

Abrasive Cleaning Particles

The liquid cleaning and/or cleansing composition herein comprise abrasive cleaning particles that are designed to feature very effective shapes, e.g. defined by macroshape and mesoshape descriptors whereas effective shape of particles are obtained by 3D printing or extruding elements with predefined cross-section and length.

The applicant has found that non-spherical and/or non-rolling and preferably sharp abrasive cleaning particles provide good soil removal and low surface damage. The applicant has found that very specific particle shapes can be obtained from extruding or 3D printing elements of material whilst having extremely good control over the final shape of the particles in order to provide accurate reproducibility of effective shapes throughout the particle population vs. the more random particles generated via for example reduction into particles from foamed structures (the latter requiring added processability in order to maintain the desired/effective shaped fraction within the population of particles).

The abrasive cleaning particles may comprise, preferably consist of, extruded, and/or three-dimensional printed, elements 1 having a longitudinal length "L" extending parallel to a z-axis and a complex cross-sectional shape extending on a plane perpendicular to said longitudinal length "L" and parallel to an x-y plane, wherein said complex cross-sectional shape comprises one or more elongate protrusions 2 each having at least one edge 3, and wherein said complex cross-sectional shape is a predetermined non-random cross-sectional shape. Most preferred are extruded elements. The latter has the benefit of lower production cost and faster particle production turnaround.

The protrusions may extend along substantially the entire length "L". This has the advantage of maximizing the scraping surface or scraping edge during scrubbing, thus increasing the amount of soil being lifted from a given surface at any given cleaning stroke.

The selection of the longitudinal length "L" is done such that there is a large number of particles lying on the surface to clean whereas the particle longitudinal length "L" is parallel to the plan of the surface to be cleaned and L is substantially perpendicular to the cleaning direction therefore yielding for a maximum cleaning efficiency If L is too short, a large number of particles will orientate on the surface to clean whereas the XY cross-sectional plan of the particles is parallel to the plan of the surface to be cleaned and the cleaning efficiency is suboptimal independently from the cleaning direction If L is too long, a large number of particles will orientate on the surface to clean whereas L is parallel to the plan of the surface to be cleaned and L is substantially parallel to the cleaning direction therefore yielding equally suboptimal cleaning efficiency The longitudinal length "L" may be dimensioned such that said elements when placed onto a surface and a cleaning force is applied in a cleaning direction spontaneously orientate themselves to deliver optimal cleaning efficiency, and wherein at least 50%, preferably at least 60%, more preferably at least 65%, even more preferably at least 70%, most preferably at least 80%, of the elements align accordingly to an orientation angle such that the length "L" is substantially perpendicular to said cleaning direction and at least a portion, preferably all, of length "L" is parallel to said surface, as measured according to the method herein. This has the advantage that at any given cleaning stroke the particles scrape the maximum soil surface.

The geometry of the XY cross-sectional plane of the particles may be dimensioned such that the particles are substantially not rolling around their Z-axis during the cleaning motion. Incidentally the cross-section of the particle is substantially irregular, preferably featuring elongated protrusions such as to increase the aspect ratio of the cross-section that minimize from partially to significantly the occurrence of the rolling phenomenon around the Z-axis of the particle. Cross-section geometries featuring at least 1 or 2 elongated protrusions are found effective whereas the extension of the elongation further reinforce the ability of the particle to avoid rolling toward the cleaning direction during the cleaning event.

The particle described here above are tailored to slide across the surface to be cleaned in an optimal motion fashion to deliver the optimal cleaning. However, the presence of at least one scrapping edge, preferably several scrapping edges along the Z-axis at the periphery of the particle cross-section, preferably with substantial sharpness as defined by a low tip radius, further optimizes the cleaning performance of the particle.

The elements may be solid, comprise a hollow core, and/or be porous. Elements with a hollow core are preferably formed by extrusion of a thermoplastic or curable material through a shaped orifice having a filled core. The resulting element typically has a cross-section which is the inverse image of the orifice. The advantage of this embodiment is that such particles may then comprise within its core an active component typically selected from cleaning actives such as surfactant, solvent, polymer acid or base, etc, or other actives such as malodor counteractants, such as reactive aldehydes, perfumes, and mixtures thereof. The latter are then gradually released upon scrubbing onto a surface. Porous elements may be generated by 3D printing a foamed structure having a predefined porosity into the desired shaped element, or by extrusion foaming through a shaped orifice. The pores may be further filled with similar active components. A further advantage of hollow and/or porous elements is that the density is greatly reduced thus enabling to suspend such particles in a liquid matrix with minimal amounts of suspending aid, whilst not compromising on cleaning performance.

The elements may be symmetrical about a plane perpendicular to said longitudinal length "L" and are preferably symmetrical or asymmetrical about a plane parallel to said longitudinal length "L". Such arrangement ensures that continuous scraping edges are formed along length "L" whilst having a very intricate cross-section to promote non-rolling around the Z-axis and optimal abrasion through the soil/surface interface.

The extruded elements may consist of one or more fibers, preferably a single continuous fiber of a material selected from organic or inorganic typically in the form of slurry based on water or solvent comprising solution, most preferably said material being a thermoplastic or thermocurable or mineral material or blend of thermoplastic and/or thermocurable and/or mineral material. The advantage of having more fibers per element is that more intricate cross-sectional shapes may be formed to increase the surface area of contact upon scrubbing onto a surface. When more fibers are used, preferably said fibers are different in that the material properties are sufficiently distinct to promote weakness points along the interface between said fibers. The latter has the advantage that the elements will tend to fracture in a specific or predetermined orientation upon the application of shear, which may be advantageous in certain applications. Preferred however are elements made of a single continuous fiber of material because of the simplicity of manufacturing process, production turnaround and lower cost.

The complex cross-sectional shape of the elements may comprise more than 2 elongate protrusions, preferably in the form of abrasive wings preferably having a shape selected from the group consisting of substantially linear, substantially concave, substantially convex and combinations thereof. This embodiment has the advantage that the elements can effectively scoop the soil from a surface.

The complex cross-sectional shape comprises from 3 to 30, preferably from 3 to 24, preferably from 3 to less than 20, more preferably from 3 to less than 15, even more preferably from 3 to less than 6, even more preferably from 3 to 4, most preferably 3, of said protrusions, preferably in the form of abrasive wings typically having a shape selected from the group consisting of substantially linear, substantially concave, substantially convex and combinations thereof. This embodiment has the advantage that resistance to rolling is further increased such that scraping is promoted.

The edge 3 (or scraping edge) may exhibit an angle of from 10° to 90°, preferably from 20° to 80°, more preferably from 30° to 60°, even more preferably from 40° to 60°. Such sharp edges ensure improved scraping of soil.

In a preferred embodiment more than 70%, preferably more than 80%, more preferably at least 90%, of the particle population exhibit the same shape of the cross-section and more than 70%, preferably more than 80%, more preferably at least 90%, of the particle population exhibit the same length. Both cross-section shape and length ensure optimal cleaning and surface safety performance.

Additionally, the abrasive particles have preferably a multitude of sharp edges. The sharp edges of the non-spherical particles are defined by edges having a tip radius below 25 µm, preferably below 8 µm, most preferably from 5 µm to 0.5 µm. The tip radius is defined by the diameter of an imaginary circle fitting the curvature of the edge extremity.

Figure 2:
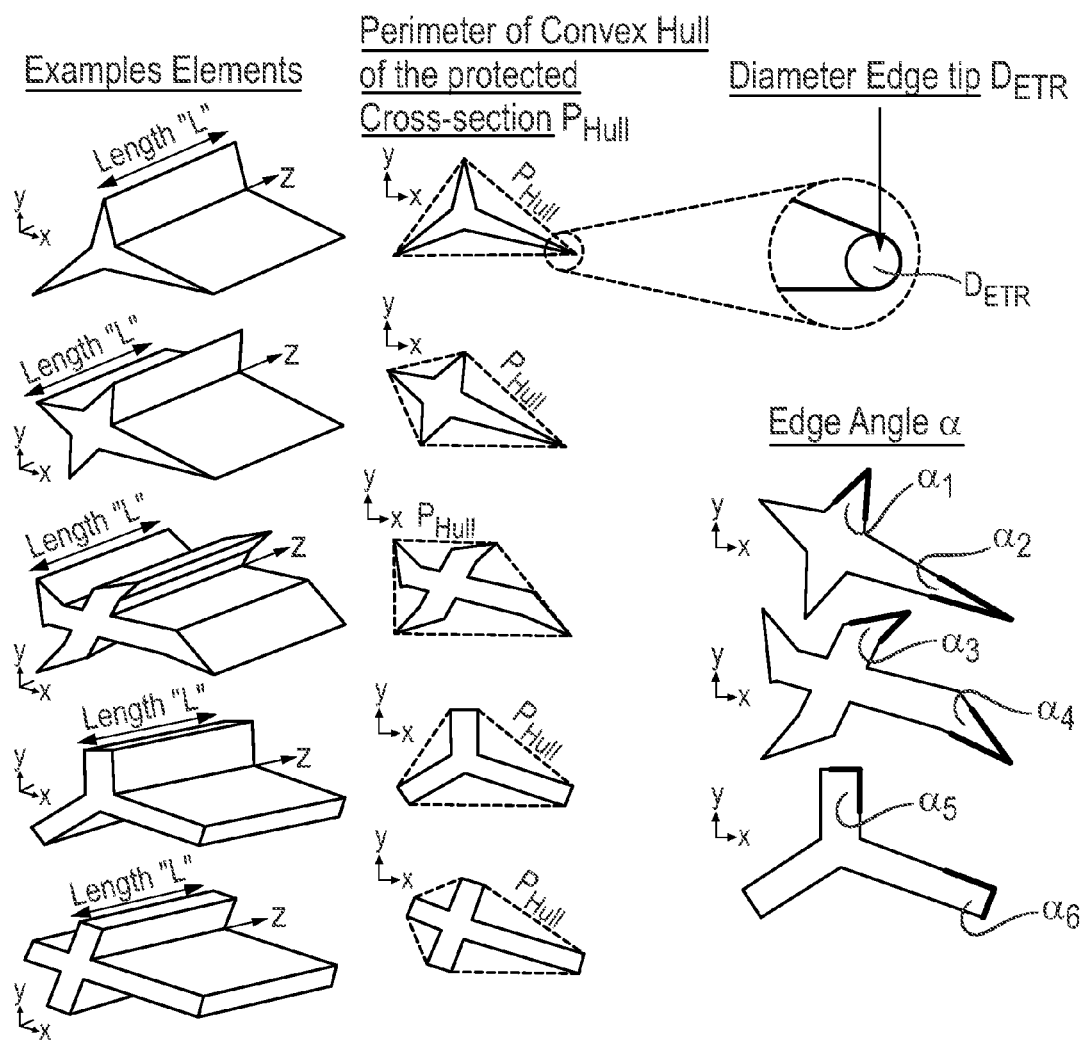
FIG. 2 is drawing showing an illustration of exemplary particles of the present invention and the respective parameters.

FIG. 2. illustrates the tip radius of exemplary particles.

In a preferred embodiment each said protrusion 2 may have at least one, preferably a single edge, having a tip radius of from greater than 0.5 µm to less than 25 µm, preferably from 1 µm to 12.5 µm, more preferably from 1 µm to 7.5 µm, equating to a tip diameter of 1 µm to less than 50 µm, preferably from 2 µm to 25 µm, more preferably from 2 µm to 15 µm. This embodiment has the advantage that improved penetration in the soil/surface interface is achieved.

Preferably the abrasive particles are made from a material comprising, preferably consisting essentially of, more preferably consisting of, a thermoplastic material, more preferably a biodegradable thermoplastic material preferably selected from the group consisting of biodegradable polyesters preferably selected from the group consisting of polyhydroxy-alkanoates preferably selected from polyhydroxyButyrate, polyhydroxyButyrate-co-valerate, polyhydroxyButyrate-co-hexanoate and mixtures thereof, poly(lactic acid), polycaprolactone, polyesteramide, aliphatic copolyesters, aromatic copolyesters, and mixtures thereof; thermoplastic starch; cellulose esters particularly cellulose acetate and/or nitrocellulose and their derivatives; and mixtures thereof; preferably a blend of a biodegradable polyester and a thermoplastic starch. More preferably the abrasive particles are made from a material comprising, preferably consisting essentially of, more preferably consisting of, a thermoplastic material, more preferably a biodegradable thermoplastic material preferably selected from the group consisting of petroleum-based polyesters preferably selected from the group consisting of polycaprolactone, polyesteramide, aliphatic copolyesters, aromatic copolyesters, and mixtures thereof; thermoplastic starch; cellulose esters particularly cellulose acetate and/or nitrocellulose and their derivatives; and mixtures thereof; preferably a blend of biodegradable petroleum-based polyester and a thermoplastic starch, preferably a blend of polycaprolactone and a thermoplastic starch. Particles made from such materials exhibit good structural properties in terms of hardness and rigidity as well as processability and effective biodegradability.

Alternatively, the abrasive particles are made from a material comprising, preferably consisting essentially of wax, preferably natural waxes such as carnauba, candellila, shellac, beewax, etc., or alternatively although less preferably of synthetic waxes such as montan, microcrystalline, polyethylene-derived wax, etc., and whereas the wax or wax blend has a high melting point, typically above 60° C., more preferably above 80° C.

Preferably, the abrasive cleaning particles consist essentially of biodegradable abrasive cleaning particles, preferably said biodegradable abrasive cleaning particles having a biodegradability rate of more than 50%, preferably more than 60%, more preferably more than 70% according to ASTM6400 test method after excluding from the degradation rate non-degrading natural or mineral material, where applicable.

Alternatively or additionally, the abrasive particles herein may comprise one or more mineral materials. Typical mineral materials of interest are derived from carbonate, sulphate, phosphate hydroxide, fluoride salts of Calcium, Barium, Iron, Magnesium, Manganese, Zinc, Copper, Borate, sodium, potassium, ammonium, alumina or silicate and blends whereas the material can be synthesized from extensively known inorganic synthesis processes (e.g.: Synthesis of Inorganic Materials—Wiley or Handbook of Inorganic Compounds—CRC) or extracted from mining & processing natural occurring inorganic material, alternatively be a mix of synthetic and natural material. Preferably, the minerals for use herein have a MOHS hardness of from 1 to 5.5, more preferably from 1.5 to 5, even more preferably from 2 to 5 and most preferably from 2.5 to 3.5 and a specific gravity of from 1 to 3, preferably a specific gravity of 1.5 to 2.5.

In case mineral material are used, slurries based on water or solvent solutions or based on blends with thermoplastic or thermoset materials are used to be extruded or 3D-printed. In cases water or solvent slurries or blends with thermosets are used, the extruded or 3D printed elements need to undergo a drying or curing treatment to solidify the mineral elements followed in most cases, although only optionally for blends with thermoplastics or thermoset, by a curing or sintering step in order to solidify the mineral-based element. Typically, the curing or sintering step range extends from 400 to 1200° C. whereas the time/temperature protocol is set to achieve the desired mechanical and hardness target.

The abrasive particles of the present invention may further comprise, at least partly incorporated therein, reinforcing filler particles that may be soluble or substantially water-insoluble. The abrasive particles having a particle size that is greater than the particle size of the filler particles. The filler particles may be sized such that to not affect the ability of the particle to orientate or to avoid rolling or separately to compromise the sharpness of the scrapping edges. In practice, it is desirable that the fillers size as defined by their mean area-equivalent diameter be below 50 µm, preferably from 0.5 to 30 µm, more preferably from 0.5 to 20 µm.

Abrasive cleaning particles comprising filler particles so sized exhibit good friability upon shear whilst still being sufficiently resistant to external stresses for good cleaning of a variety of soils on a variety of surfaces. Moreover, such filler particles enable more effective biodegradation of the abrasive particles.

When the filler particles used comprise a material selected from natural mineral materials such as talk, mica, barium sulfate, wood, walnut, kaolin and the like, the biodegradability rate is calculated based on the biodegradation of the abrasive particle excluding the actual filler. In a preferred embodiment the filler particles comprise a material selected from the group consisting of organic, in-organic and mixtures thereof. Preferably the organic material is selected from vegetal feedstock essentially cellulose or lignocellulose based material e.g.: nut shell, wood, cotton flax or bamboo fibers, corn cob, rice hull, sugars and more generally carbohydrate especially starch from corn, maize, potato, alternatively urea, etc; other plant parts selected from the group consisting of stems, roots, leaves, seeds, and mixtures thereof.

In a preferred embodiment, especially when the matrix material is made of thermoplastic with high crystallinity, the filler is made of starch with high content of amylose and low content of amylopectin (by "low" it is meant less than 10%, preferably less than 5%, more preferably less than 1%, by weight of the starch). Indeed, the amylose are typically low branched carbohydrate that allow fast and efficient crystallisation of the thermoplastic hence promoting better foam formation and material with better mechanical and chemical resilience. Typically, starch filler with amylose content above 30%, preferably above 50% are especially preferred since such have been found not to prevent or significantly reduce the rate of crystallization leading to particles with better strength and shape.

The fillers may be selected from in-organic material wherein the inorganic material is having a specific gravity of from 1 to 3 and mohs hardness comprised between 1-5.5. Suitable example of in-organic fillers are derived from sulfate, or carbonate metal salts, such as $Ca_2CO_3$, $MgSO_4$, barite, generally phyllosilicate material e.g.; talc, kaolinite, vermiculite, mica, muscovite, pyrophillite, bentonite, montmorrillonite, feldspar, etc, and mixtures thereof.

Alternatively or in addition, non-biodegradable polymeric reinforcing fillers may be used, although it is preferred not to use them in high quantities when substantial biodegradation level of the abrasive particles is desired. In this case, non-biodegradable polymers can be used in quantity not exceeding 10% of the weight of the biodegradable polymer. Suitable non-biodegradable polymeric fillers can be selected from the group consisting of polyethylene, polypropylene, polystyrene, polyvinyl chloride (PVC), polyacrylate, non-biodegradable polyurethane, and their derivatives and mixtures thereof.

It is highly preferred that the reinforcing filler particles, when used, are comprised at a level of from 5% to 70%, preferably from 10% to 60%, preferably from greater than 15% to 60%, more preferably from 20% to 60%, most preferably from greater than 30% to 60%, by weight of the abrasive particle. Such high levels of filler particles enables to reduce the cost of the abrasives as well as still meeting the structural requirements and improving biodegradability when needed.

In a preferred embodiment, the reinforcing filler particles are incorporated into the abrasive cleaning particles in such a way that at least part of said filler particles does not protrude significantly out of the surface of said abrasive particles in order to not compromise the sharpness of the scrapping edges or the pre-defined geometry of the elements.

The applicant has surprisingly further discovered that efficient cleaning result can be achieved with particle population occupying a large volume per mass of particles loaded in a cleaning composition. The volume that the particles will occupy is defined by the packing density of the particles. The packing density of a particle population represents the mass of a sample of particle population divided by the volume occupied by the particles sample measured in dry condition after packing with normal gravity force. Incidentally, a particle population with low packing density will occupy a high volume, both in cleaner and during cleaning operation to provide effective cleaning performance, while a particle sample with high packing density will occupy a low volume, both in cleaner and during cleaning operation hence providing low effective cleaning performance.

Indeed, particles with low packing density are effective at providing maximum contact area between the abrasive particles and the soil and/or surface to be cleaned. And therefore, lower quantity of abrasive particles can be used in cleaning composition i.e., below 10% vs. commonly above 20%, while delivering equal or better cleaning effectiveness. It is commonly known, that higher quantity of particles in the cleaning composition leads to a better cleaning effectiveness, additionally a higher mass of particle was used to maximize the cleaning performance. The applicant has established that the cleaning efficiency is rather impacted by the volume that the abrasive population occupies at the cleaning interface versus typically the mass of the abrasive population. Incidentally, particles with low packing density typically require lower mass load of the abrasive in the cleaner versus high packing density particles to produce efficient cleaning.

The applicant has found that abrasive population with high packing density feature low cleaning performance while, on the other hand, abrasive population with lower packing density has intrinsic fragility that is also inadequate for cleaning purpose via mechanical abrasion. In a preferred embodiment the abrasive particles have a packing density of from 50 $kg/m^3$ to 400 $kg/m^3$, preferably from 60 $kg/m^3$ to 250 $kg/m^3$, more preferably from 80 $kg/m^3$ to 200 $kg/m^3$, even more preferably from 90 $kg/m^3$ to 150 $kg/m^3$. Such particles are providing good cleaning performance and surface safety.

The packing density herein is calculated according to the following method: One tenth of a gram (0.1 g+/−0.001 g) of dry particles is placed into a 20 ml precise metric graduated Pyrex® volumetric cylinder (as available from Sigma-Aldrich). The cylinder is sealed (e.g. with a stopper or film), and subsequently shaken using a Vortex mixer (for example, the model L-46 Power Mix from Labinco DNTE SP-016) at 2500 rpm (maximum speed) for 30 seconds. The volume of the particles is measured after vibration. If the volume is between 5 to 15 ml, this is converted accordingly into packing density as expressed in kg/m3. If the volume of 0.1 g is less than 5 ml, then two tenths of a gram (0.2 g+/−0.001 g) of dry particles is used to re-run the test in clean cylinder. If the volume of the 0.2 g is less than 5 ml, then half a gram (0.5 g+/−0.001 g) of dry particles is used to re-run the test in a clean cylinder. If the volume of the 0.5 g is less than 5 ml, then one gram (1.0 g+/−0.001 g) of dry particles is used to re-run the test in a clean cylinder, with volumes between 3 to 15 ml converted into kg/m3 for packing density.

Preferred abrasive cleaning particles suitable for used herein are hard enough to provide good cleaning/cleansing performance, whilst providing a good surface safety profile. The hardness of the abrasive particles can be modified by changing the raw material used to prepare them.

In a preferred embodiment the abrasive cleaning particles have a hardness expressed accordingly to the MOHS hardness scale. Preferably, the MOHS hardness is comprised between 1 and 5.5, preferably is from 1.5 to 5, more preferably from 2 to 4, and most preferably from 2.5 to 3. The MOHS hardness scale is an internationally recognized scale for measuring the hardness of a compound versus a compound of known hardness, see Encyclopedia of Chemical Technology, Kirk-Othmer, 4 th Edition Vol 1, page 18 or Lide, D. R (ed) CRC Handbook of Chemistry and Physics, 73 rd edition, Boca Raton, Fla.: The Rubber Company, 1992-1993. Many MOHS Test kits are commercially available containing material with known MOHS hardness. For measurement and selection of abrasive material with selected MOHS hardness, it is recommended to execute the MOHS hardness measurement with un-shaped particles e.g.: with spherical or granular forms of the abrasive material since MOHS measurement of shape particles will provide erroneous results.

In one preferred example, the size of the abrasive cleaning particles used in the present invention is modified during usage especially undergoing significant size reduction. Hence the particle remain visible or tactile detectable in liquid composition and at the start of the usage process to provide effective cleaning. As the cleaning process progresses, the abrasive particles disperse or break into smaller particles and become invisible to an eye or tactile undetectable. This effect is better improved by the incorporation of filler particles of the present invention.

It has surprisingly been found that the abrasive cleaning particles of the present invention show a good cleaning performance even at relatively low levels, such as preferably from 0.1% to 10% by weight of the total composition, preferably from 0.1% to 5%, more preferably from 0.5% to less than 5%, even more preferably from 1.0% to 3%, by weight of the total composition of said abrasive cleaning particles.

The particles used in the present invention can be white, transparent or colored by use of suitable dyes and/or pigments. Additionally suitable color stabilizing agents can be used to stabilize desired color. The abrasive particles are preferable color stable particles. By "color stable" it is meant herein that color of the particles used in the present invention will not turn yellow during storage and use.

In one preferred example, the abrasive cleaning particles used in the present invention remain visible when liquid composition is stored into a bottle while during the effective cleaning process abrasive particles disperse or break into smaller particles and become invisible to an eye.

The applicant has found that efficacious and safe cleaning particles can be produced with very specific structural and shape parameters as described below. The determination of the shape factors discussed below are accessible from using for instance the Occhio Nano 500 or in Malvern Morphologi G3.

Form Factor:

Form factor is a preferred mesoshape descriptor and is a quantitative, 2-dimension image analysis shape description and is being measured according to ISO 9276-6:2008(E) section 8.2. Form factor is sometimes described in literature as being the difference between a particle's shape and a perfect sphere. Form factor values range from 0 to 1, where a form factor of 1 describes a perfectly spherical particles or disc particle as measured in a two dimensional image.

$$\text{Form Factor} = \frac{4\pi A}{P^2}$$

Where A is projection area, which is 2D descriptor and P is the length of the perimeter of the particle. The applicants refer herein to mean data, wherein mean data are extracted from volume-based vs. number-based measurements The elements herein may have a predetermined shape having a form factor, preferably a mean form factor, of from 0.3 to 0.8 preferably from 0.5 to 0.75, preferably from 0.55 to 0.65.

The elements herein may have a predetermined cross-sectional shape projected along the Z-axe of the element having a form factor, preferably a mean form factor, of from 0.1 to 0.7 preferably from 0.1 to 0.5, preferably from 0.15 to 0.35 and more preferably from 0.2 to 0.3.

Solidity:

Solidity is a quantitative, 2-dimensional image analysis shape description, and is being measured according to ISO 9276-6:2008(E) section 8.2. Solidity is a mesoshape parameter, which describes the overall concavity of a particle/particle population. Solidity values range from 0 to 1, where a solidity number of 1 describes a non-concave particle, as measured in literature as being:

Solidity=$A/Ac$

Where A is the area of the particle and Ac (or Ahull) is the area of the convex hull (envelope) of bounding the particle. The applicants refer herein to mean data, wherein mean data are extracted from volume-based vs. number-based measurements The elements herein may have a predetermined shape having a solidity, preferably a mean solidity from greater than 0.85 to 1, preferably from 0.90 to 1, preferably from 0.95 to 1.

The elements herein may have a predetermined cross-sectional shape projected along the Z-axe of the element having a solidity, preferably a mean solidity, of from 0.2 to 0.8, preferably from 0.35 to 0.75, preferably from 0.4 to 0.7, and more preferably from 0.5 to 0.65.

The abrasive particles may have a particle solidity of from 0.85 to 1, preferably from 0.9 to 1, more preferably from 0.95 to 1, and a particle form factor of from 0.3 to 0.8, according to ISO 9276-6.

Solidity is sometime also named Convexity in literature or in some apparatus software using the solidity formula in place of its definition described in ISO 9276-6 (convexity=Pc/P where P is the length of the perimeter of the particle and $P_C$ or $P_{hull}$ is length of the perimeter of the convex hull—envelope—bounding the particle or element cross section). Despite solidity and convexity being similar mesoshape descriptor in concept, the applicant refers herein to the solidity measure expressed to the definition herein.

Feret diameters $F_{max}$ and $F_{min}$:

The Feret diameter is a geometrical shape descriptor based on the distance between parallel tangents of a particle's shape. Such descriptor essentially defines the elongation of the particle with respect to maximum and minimum parallel tangent diameters. The maximum diameter $F_{max}$ corresponds to the "length" of the particle and the minimum diameter $F_{min}$ corresponds to the "breadth" of the particle, and is measured according to ISO 9276-6:2008(E) section 8.1.2.

The particles, in particular the cross-section projected along the Z-axe of the elements herein, may have a maximum Feret diameter $F_{max}$ of from 100 µm to 800 µm, preferably from 200 µm to 500 µm, more preferably from 250 µm to 400 µm, and a minimum Feret diameter $F_{min}$ of from 50 µm to 350 µm. The applicants identified that this combination of values of both the Feret diameters $F_{max}$ and $F_{min}$ are optimal for typical 3-body cleaning systems and mechanisms observed in homecare or beautycare cleaning occurrence given the size or thickness of the typical soils and soil layers, the typical roughness topography of the surfaces to clean and especially the typical porosity of the cleaning implement such as natural or synthetic sponge or paper or nonwoven substrates.

In an alternative embodiment, particularly for certain applications such as oral care, the particles, in particular the cross-section projected along the Z-axe of the elements herein, may have a maximum Feret diameter $F_{max}$ of from 5 µm to 50 µm, preferably from 8 µm to 30 µm, more preferably from 10 µm to 25 µm, and a minimum Feret diameter $F_{min}$ of from 2 µm to 15 µm. The applicants identified that this combination of values of both the Feret diameters $F_{max}$ and $F_{min}$ are optimal in for typical 3-body cleaning systems and mechanisms observed in oral care cleaning especially to achieve a good compromise between an efficient cleaning and a comfortable feel sensation in mouth inherent to the size and shape of the particles.

Aspect Ratio $F_{min}/F_{max}$

The aspect ratio as defined in ISO 9276-6:2008(E) section 8.1.3. The applicants are defining the aspect ratio of being the ratio of the Feret diameters Fmin/Fmax of the cross-sectional shape projected along the Z-axe of the element, preferably the mean aspect ratio of all particles. The applicants found that the effective aspect ratio needed to prevent the particle(s) from rolling around it (their) Z-axe(s) during the cleaning event, is substantially below 1, preferably from 0.1 to 0.7, preferably from 0.2 to 0.6, more preferably from 0.3 to 0.55, more preferably from 0.35 to 0.55.

Area-Equivalent Diameter "ECD":

The area-equivalent diameter of the elements herein (ISO 9276-6:2008(E) section 7) also called Equivalent Circle Diameter "ECD" (ASTM F1877-05 Section 11.3.2) is calculated by following the method herein, preferably according to ISO 9276-6:2008(E) section 7.

The area-equivalent diameter "ECD", preferably the mean area-equivalent diameter "mean $ECD_1$", of the elements herein may be from 100 µm to 800 µm, preferably from 100 µm to 500 µm, more preferably from 150 µm to 350 µm, even more preferably from 200 µm to 300 µm. Alternatively for some applications such as for oral care, the area-equivalent diameter "ECD", preferably the mean area-equivalent diameter "mean ECD" of the elements herein may be from 5 µm to 50 µm, preferably from 5 µm to 30 µm, more preferably from 5 to 20 µm.

Perimeter-Equivalent Diameter "ECD $P_{Hull}$".

The perimeter-equivalent diameter "ECD $P_{Hull}$" is the diameter of a circle having a perimeter equivalent to $P_{Hull}$ whereas $P_{Hull}$ is the length of the perimeter of the convex hull (envelope) bounding the particle (ISO 9276-6:2008).

The perimeter-equivalent diameter "ECD $P_{Hull}$", preferably the mean perimeter-equivalent diameter "mean ECD $P_{Hull}$", of the cross-sectional shape projected along the Z-axe of the elements herein may be from 100 µm to 800 µm, preferably from 150 µm to 350 µm more preferably from 200 µm to 300 µm. Alternatively for some applications such as for oral care, the perimeter-equivalent diameter "ECD $P_{Hull}$", preferably the mean perimeter-equivalent diameter "mean ECD $P_{Hull}$", of the cross-sectional shape projected along the Z-axe of the elements herein may be from 2 µm to 50 µm, preferably from 5 µm to 20 µm.

Ratio L/ECD $P_{Hull}$:

The ratio L to ECD $P_{Hull}$, is an effective parameter defining the particle's ability to effectively orient for optimal cleaning and scraping of soil from a surface.

In a preferred embodiment elements herein have a ratio L to ECD $P_{Hull}$, preferably a ratio mean L to mean ECD $P_{Hull}$, of from 0.5 to 3, preferably from 0.8 to 2.5, more preferably from 1 to 2, even more preferably from 1.3 to 1.7. The advantage of this embodiment is that of improved cleaning and surface safety effectiveness.

By the term "mean form factor" or "mean solidity", "mean Feret diameters", "mean Area-equivalent diameter", "mean Perimeter-equivalent diameter", etc., the applicant consider the average of the values of each particle taken from a population of at least 1000, preferably above 10 000 particles, preferably above 50 000 particles, more preferably above 100 000 particles, including particles having area-equivalent diameter (ECD) of above 10 microns for general applications purposes except for oral care purpose whereas particles having area-equivalent diameter (ECD) of above 1 microns are included in the computation. Mean data are extracted from volume-based vs. number-based measurements.

Optionally, the particles with above defined mesoshape descriptors may be mixed with more granular/spherical type of abrasives. In that case, the applicant considers the value range as described above to apply to the final mix.

Optional Ingredients

The compositions according to the present invention may comprise a variety of optional ingredients depending on the technical benefit aimed for and the surface treated.

Suitable optional ingredients for use herein include chelating agents, surfactants, radical scavengers, perfumes, surface-modifying polymers, solvents, builders, buffers, bactericides, hydrotropes, colorants, stabilizers, bleaches, bleach activators, suds controlling agents like fatty acids, enzymes, soil suspenders, brighteners, anti dusting agents, dispersants, pigments, and dyes.

Suspending Aid

The abrasive cleaning particles present in the composition herein are solid particles in a liquid composition. Said abrasive cleaning particles may be suspended in the liquid composition. However, it is well within the scope of the present invention that such abrasive cleaning particles are not-stably suspended within the composition and either settle or float on top of the composition. In this case, a user may have to temporally suspend the abrasive cleaning particles by agitating (e.g., shaking or stirring) the composition prior to use.

However, it is preferred herein that the abrasive cleaning particles are stably suspended in the liquid compositions herein. Thus the compositions herein comprise a suspending aid.

The suspending aid herein may either be a compound specifically chosen to provide a suspension of the abrasive cleaning particles in the liquid compositions of the present invention, such as a structurant, or a compound that also provides another function, such as a thickener or a surfactant (as described herein elsewhere).

Any suitable organic and inorganic suspending aids typically used as gelling, thickening or suspending agents in cleaning/cleansing compositions and other detergent or cosmetic compositions may be used herein. Indeed, suitable organic suspending aids include polysaccharide polymers. In addition or as an alternative, polycarboxylate polymer thickeners may be used herein. Also, in addition or as an alternative of the above, layered silicate platelets e.g.: Hectorite, bentonite or montmorillonites can also be used. Suitable commercially available layered silicates are Laponite RD® or Optigel CL® available from Rockwood Additives.

Suitable polycarboxylate polymer thickeners include (preferably lightly) crosslinked polyacrylate. A particularly suitable polycarboxylate polymer thickeners is Carbopol commercially available from Lubrizol under the trade name Carbopol 674®.

Suitable polysaccharide polymers for use herein include substituted cellulose materials like carboxymethylcellulose, ethyl cellulose, hydroxyethyl cellulose, hydroxypropyl cellulose, hydroxymethyl cellulose, succinoglycan and naturally occurring polysaccharide polymers like Xanthan gum, gellan gum, guar gum, locust bean gum, tragacanth gum, succinoglucan gum, or derivatives thereof, or mixtures thereof. Xanthan gum is commercially available from Kelco under the tradename Kelzan T.

Preferably the suspending aid herein is Xanthan gum. In an alternative embodiment, the suspending aid herein is a polycarboxylate polymer thickeners preferably a (preferably lightly) crosslinked polyacrylate. In a highly preferred embodiment herein, the liquid compositions comprise a combination of a polysaccharide polymer or a mixture thereof, preferably Xanthan gum, with a polycarboxylate polymer or a mixture thereof, preferably a crosslinked polyacrylate. As a preferred example, Xanthan gum is preferably present at levels between 0.1% to 5% by weight of the total composition, more preferably from 0.5% to 2%, even more preferably from 0.8% to 1.2%.

Organic Solvent

As an optional but highly preferred ingredient the composition herein comprises an organic solvents or mixtures thereof.

The compositions herein comprise from 0% to 30% by weight of the total composition of an organic solvent or a mixture thereof, more preferably 1.0% to 20% and most preferably, 2% to 15%.

Suitable solvents can be selected from the group consisting of: aliphatic alcohols, ethers and diethers having from 4 to 14 carbon atoms, preferably from 6 to 12 carbon atoms, and more preferably from 8 to 10 carbon atoms; glycols or alkoxylated glycols; glycol ethers; alkoxylated aromatic alcohols; aromatic alcohols; terpenes; and mixtures thereof. Aliphatic alcohols and glycol ether solvents are most preferred.

Aliphatic alcohols, of the formula R—OH wherein R is a linear or branched, saturated or unsaturated alkyl group of from 1 to 20 carbon atoms, preferably from 2 to 15 and more preferably from 5 to 12, are suitable solvents. Suitable aliphatic alcohols are methanol, ethanol, propanol, isopropanol or mixtures thereof. Among aliphatic alcohols, ethanol and isopropanol are most preferred because of their high vapour pressure and tendency to leave no residue.

Suitable glycols to be used herein are according to the formula HO—$CR_1R_2$—OH wherein R1 and R2 are independently H or a $C_2$-$C_{10}$ saturated or unsaturated aliphatic hydrocarbon chain and/or cyclic. Suitable glycols to be used herein are dodecaneglycol and/or propanediol.

In one preferred embodiment, at least one glycol ether solvent is incorporated in the compositions of the present invention. Particularly preferred glycol ethers have a terminal $C_3$-$C_6$ hydrocarbon attached to from one to three ethylene glycol or propylene glycol moieties to provide the appropriate degree of hydrophobicity and, preferably, surface activity. Examples of commercially available solvents based on ethylene glycol chemistry include mono-ethylene glycol n-hexyl ether (Hexyl Cellosolve®) available from Dow Chemical. Examples of commercially available solvents based on propylene glycol chemistry include the di-, and tri-propylene glycol derivatives of propyl and butyl alcohol, which are available from Arco under the trade names Arcosolv® and Dowanol®.

In the context of the present invention, preferred solvents are selected from the group consisting of mono-propylene glycol mono-propyl ether, di-propylene glycol mono-propyl ether, mono-propylene glycol mono-butyl ether, di-propylene glycol mono-propyl ether, di-propylene glycol mono-butyl ether; tri-propylene glycol mono-butyl ether; ethylene glycol mono-butyl ether; di-ethylene glycol mono-butyl ether, ethylene glycol mono-hexyl ether and di-ethylene glycol mono-hexyl ether, and mixtures thereof. "Butyl" includes normal butyl, isobutyl and tertiary butyl groups. Mono-propylene glycol and mono-propylene glycol mono-butyl ether are the most preferred cleaning solvent and are available under the tradenames Dowanol DPnP® and Dowanol DPnB®. Di-propylene glycol mono-t-butyl ether is commercially available from Arco Chemical under the tradename Arcosolv PTB®.

In a particularly preferred embodiment, the cleaning solvent is purified so as to minimize impurities. Such impurities include aldehydes, dimers, trimers, oligomers and other by-products. These have been found to deleteriously affect product odour, perfume solubility and end result. The inventors have also found that common commercial solvents, which contain low levels of aldehydes, can cause irreversible and irreparable yellowing of certain surfaces. By purifying the cleaning solvents so as to minimize or eliminate such impurities, surface damage is attenuated or eliminated.

Though not preferred, terpenes can be used in the present invention. Suitable terpenes to be used herein monocyclic terpenes, dicyclic terpenes and/or acyclic terpenes. Suitable terpenes are: D-limonene; pinene; pine oil; terpinene; terpene derivatives as menthol, terpineol, geraniol, thymol; and the citronella or citronellol types of ingredients.

Suitable alkoxylated aromatic alcohols to be used herein are according to the formula R-(A)$_n$-OH wherein R is an alkyl substituted or non-alkyl substituted aryl group of from 1 to 20 carbon atoms, preferably from 2 to 15 and more preferably from 2 to 10, wherein A is an alkoxy group preferably butoxy, propoxy and/or ethoxy, and n is an integer of from 1 to 5, preferably 1 to 2. Suitable alkoxylated aromatic alcohols are benzoxyethanol and/or benzoxypropanol.

Suitable aromatic alcohols to be used herein are according to the formula R—OH wherein R is an alkyl substituted or non-alkyl substituted aryl group of from 1 to 20 carbon atoms, preferably from 1 to 15 and more preferably from 1 to 10. For example a suitable aromatic alcohol to be used herein is benzyl alcohol.

Surfactants

The compositions herein may comprise a nonionic, anionic, zwitterionic, cationic and amphoteric surfactant or mixtures thereof. Suitable surfactants are those selected from the group consisting of nonionic, anionic, zwitterionic, cationic and amphoteric surfactants, having hydrophobic chains containing from 8 to 18 carbon atoms. Examples of suitable surfactants are described in McCutcheon's Vol. 1: Emulsifiers and Detergents, North American Ed., McCutcheon Division, MC Publishing Co., 2002.

Preferably, the composition herein comprises from 0.01% to 20% by weight of the total composition of a surfactant or a mixture thereof, more preferably from 0.5% to 10%, and most preferably from 1% to 5%.

Non-ionic surfactants are highly preferred for use in the compositions of the present invention. Non-limiting examples of suitable non-ionic surfactants include alcohol alkoxylates, alkyl polysaccharides, amine oxides, block copolymers of ethylene oxide and propylene oxide, fluoro surfactants and silicon based surfactants. Preferably, the aqueous compositions comprise from 0.01% to 20% by weight of the total composition of a non-ionic surfactant or a mixture thereof, more preferably from 0.5% to 10%, and most preferably from 1% to 5%.

A preferred class of non-ionic surfactants suitable for the present invention is alkyl ethoxylates. The alkyl ethoxylates of the present invention are either linear or branched, and contain from 8 carbon atoms to 16 carbon atoms in the hydrophobic tail, and from 3 ethylene oxide units to 25 ethylene oxide units in the hydrophilic head group. Examples of alkyl ethoxylates include Neodol 91-6®, Neodol 91-8® supplied by the Shell Corporation (P.O. Box 2463, 1 Shell Plaza, Houston, Tex.), and Alfonic 810-60® supplied by Condea Corporation, (900 Threadneedle P.O. Box 19029, Houston, Tex.). More preferred alkyl ethoxylates comprise from 9 to 12 carbon atoms in the hydrophobic tail, and from 4 to 9 oxide units in the hydrophilic head group. A most preferred alkyl ethoxylate is $C_{9-11}$ $EO_5$, available from the Shell Chemical Company under the tradename Neodol 91-5®. Non-ionic ethoxylates can also be derived from branched alcohols. For example, alcohols can be made from branched olefin feedstocks such as propylene or butylene. In a preferred embodiment, the branched alcohol is either a 2-propyl-1-heptyl alcohol or 2-butyl-1-octyl alcohol. A desirable branched alcohol ethoxylate is 2-propyl-1-heptyl EO7/AO7, manufactured and sold by BASF Corporation under the tradename Lutensol XP 79/XL 79®.

Another class of non-ionic surfactant suitable for the present invention is alkyl polysaccharides. Such surfactants are disclosed in U.S. Pat. Nos. 4,565,647, 5,776,872, 5,883,062, and 5,906,973. Among alkyl polysaccharides, alkyl polyglycosides comprising five and/or six carbon sugar rings are preferred, those comprising six carbon sugar rings are more preferred, and those wherein the six carbon sugar ring is derived from glucose, i.e., alkyl polyglucosides ("APG"), are most preferred. The alkyl substituent in the APG chain length is preferably a saturated or unsaturated alkyl moiety containing from 8 to 16 carbon atoms, with an average chain length of 10 carbon atoms. $C_8$-$C_{16}$ alkyl polyglucosides are commercially available from several suppliers (e.g., Simusol® surfactants from Seppic Corporation, 75 Quai d'Orsay, 75321 Paris, Cedex 7, France, and Glucopon 220®, Glucopon 225®, Glucopon 425®, Plantaren 2000 N®, and Plantaren 2000 N UP®, from Cognis Corporation, Postfach 13 01 64, D 40551, Dusseldorf, Germany).

Another class of non-ionic surfactant suitable for the present invention is amine oxide. Amine oxides, particularly those comprising from 10 carbon atoms to 16 carbon atoms in the hydrophobic tail, are beneficial because of their strong cleaning profile and effectiveness even at levels below 0.10%. Additionally $C_{10-16}$ amine oxides, especially $C_{12}$-$C_{14}$ amine oxides are excellent solubilizers of perfume. Alternative non-ionic detergent surfactants for use herein are alkoxylated alcohols generally comprising from 8 to 16 carbon atoms in the hydrophobic alkyl chain of the alcohol. Typical alkoxylation groups are propoxy groups or ethoxy groups in combination with propoxy groups, yielding alkyl ethoxy propoxylates. Such compounds are commercially available under the tradename Antarox® available from Rhodia (40 Rue de la Haie-Coq F-93306, Aubervilliers Cédex, France) and under the tradename Nonidet® available from Shell Chemical.

The condensation products of ethylene oxide with a hydrophobic base formed by the condensation of propylene oxide with propylene glycol are also suitable for use herein. The hydrophobic portion of these compounds will preferably have a molecular weight of from 1500 to 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to 40 moles of ethylene oxide. Examples of compounds of this type include certain of the commercially available Pluronic® surfactants, marketed by BASF. Chemically, such surfactants have the structure $(EO)_x(PO)_y(EO)_z$ or $(PO)_x(EO)_y(PO)_z$ wherein x, y, and z are from 1 to 100, preferably 3 to 50. Pluronic® surfactants known to be good wetting surfactants are more preferred. A description of the Pluronic® surfactants, and properties thereof, including wetting properties, can be found in the brochure entitled "BASF Performance Chemicals Plutonic® & Tetronic® Surfactants", available from BASF.

Other suitable though not preferred non-ionic surfactants include the polyethylene oxide condensates of alkyl phenols, e.g., the condensation products of alkyl phenols having an alkyl group containing from 6 to 12 carbon atoms in either a straight chain or branched chain configuration, with ethylene oxide, the said ethylene oxide being present in amounts equal to 5 to 25 moles of ethylene oxide per mole of alkyl phenol. The alkyl substituent in such compounds can be derived from oligomerized propylene, diisobutylene, or from other sources of iso-octane n-octane, iso-nonane or n-nonane. Other non-ionic surfactants that can be used include those derived from natural sources such as sugars and include $C_8$-$C_{16}$ N-alkyl glucose amide surfactants.

Suitable anionic surfactants for use herein are all those commonly known by those skilled in the art. Preferably, the anionic surfactants for use herein include alkyl sulphonates, alkyl aryl sulphonates, alkyl sulphates, alkyl alkoxylated sulphates, $C_6$-$C_{20}$ alkyl alkoxylated linear or branched diphenyl oxide disulphonates, or mixtures thereof.

Suitable alkyl sulphonates for use herein include water-soluble salts or acids of the formula $RSO_3M$ wherein R is a $C_6$-$C_{20}$ linear or branched, saturated or unsaturated alkyl group, preferably a $C_8$-$C_{18}$ alkyl group and more preferably a $C_{10}$-$C_{16}$ alkyl group, and M is H or a cation, e.g., an alkali metal cation (e.g., sodium, potassium, lithium), or ammonium or substituted ammonium (e.g., methyl-, dimethyl-, and trimethyl ammonium cations and quaternary ammonium cations, such as tetramethyl-ammonium and dimethyl piperdinium cations and quaternary ammonium cations derived from alkylamines such as ethylamine, diethylamine, triethylamine, and mixtures thereof, and the like).

Suitable alkyl aryl sulphonates for use herein include water-soluble salts or acids of the formula $RSO_3M$ wherein R is an aryl, preferably a benzyl, substituted by a $C_6$-$C_{20}$ linear or branched saturated or unsaturated alkyl group, preferably a $C_8$-$C_{18}$ alkyl group and more preferably a $C_{10}$-$C_{16}$ alkyl group, and M is H or a cation, e.g., an alkali metal cation (e.g., sodium, potassium, lithium, calcium, magnesium and the like) or ammonium or substituted ammonium (e.g., methyl-, dimethyl-, and trimethyl ammonium cations and quaternary ammonium cations, such as tetramethyl-ammonium and dimethyl piperdinium cations and quaternary ammonium cations derived from alkylamines such as ethylamine, diethylamine, triethylamine, and mixtures thereof, and the like).

An example of a $C_{14}$-$C_{16}$ alkyl sulphonate is Hostapur® SAS available from Hoechst. An example of commercially available alkyl aryl sulphonate is Lauryl aryl sulphonate from Su.Ma. Particularly preferred alkyl aryl sulphonates are alkyl benzene sulphonates commercially available under trade name Nansa® available from Albright & Wilson.

Suitable alkyl sulphate surfactants for use herein are according to the formula $R_1SO_4M$ wherein $R_1$ represents a hydrocarbon group selected from the group consisting of straight or branched alkyl radicals containing from 6 to 20 carbon atoms and alkyl phenyl radicals containing from 6 to 18 carbon atoms in the alkyl group. M is H or a cation, e.g., an alkali metal cation (e.g., sodium, potassium, lithium, calcium, magnesium and the like) or ammonium or substituted ammonium (e.g., methyl-, dimethyl-, and trimethyl ammonium cations and quaternary ammonium cations, such as tetramethyl-ammonium and dimethyl piperdinium cations and quaternary ammonium cations derived from alkylamines such as ethylamine, diethylamine, triethylamine, and mixtures thereof, and the like). Particularly preferred branched alkyl sulphates to be used herein are those containing from 10 to 14 total carbon atoms like Isalchem 123 AS®. Isalchem 123 AS® commercially available from Enichem is a $C_{12}$-$C_{13}$ surfactant which is 94% branched. This material can be described as $CH_3$—$(CH_2)_m$—CH$(CH_2OSO_3Na)$—$(CH_2)_n$—$CH_3$ where n+m=8-9. Also preferred alkyl sulphates are the alkyl sulphates where the alkyl chain comprises a total of 12 carbon atoms, i.e., sodium 2-butyl octyl sulphate. Such alkyl sulphate is commercially available from Condea under the trade name Isofol® 12S. Particularly suitable liner alkyl sulphonates include $C_{12}$-$C_{16}$ paraffin sulphonate like Hostapur® SAS commercially available from Hoechst.

Suitable alkyl alkoxylated sulphate surfactants for use herein are according to the formula $RO(A)_mSO_3M$ wherein R is an unsubstituted $C_6$-$C_{20}$ alkyl or hydroxyalkyl group having a $C_6$-$C_{20}$ alkyl component, preferably a $C_{12}$-$C_{20}$ alkyl or hydroxyalkyl, more preferably $C_{12}$-$C_{18}$ alkyl or hydroxyalkyl, A is an ethoxy or propoxy unit, m is greater than zero, typically between 0.5 and 6, more preferably between 0.5 and 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl-, trimethyl-ammonium and quaternary ammonium cations, such as tetramethyl-ammonium, dimethyl piperdinium and cations derived from alkanolamines such as ethylamine, diethylamine, triethylamine, mixtures thereof, and the like. Exemplary surfactants are $C_{12}$-$C_{18}$ alkyl polyethoxylate (1.0) sulfate ($C_{12}$-$C_{18}$E(1.0)SM), $C_{12}$-$C_{18}$ alkyl polyethoxylate (2.25) sulfate ($C_{12}$-$C_{18}$E(2.25)SM), $C_{12}$-$C_{18}$ alkyl polyethoxylate (3.0) sulfate ($C_{12}$-$C_{18}$E(3.0)SM), $C_{12}$-$C_{18}$ alkyl polyethoxylate (4.0) sulfate ($C_{12}$-$C_{18}$E (4.0)SM), wherein M is conveniently selected from sodium and potassium.

Suitable $C_6$-$C_{20}$ alkyl alkoxylated linear or branched diphenyl oxide disulphonate surfactants for use herein are according to the following formula:

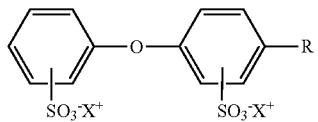

wherein R is a $C_6$-$C_{20}$ linear or branched, saturated or unsaturated alkyl group, preferably a $C_{12}$-$C_{18}$ alkyl group and more preferably a $C_{14}$-$C_{16}$ alkyl group, and X+ is H or a cation, e.g., an alkali metal cation (e.g., sodium, potassium, lithium, calcium, magnesium and the like). Particularly suitable $C_6$-$C_{20}$ alkyl alkoxylated linear or branched diphenyl oxide disulphonate surfactants to be used herein are the $C_{12}$ branched di phenyl oxide disulphonic acid and $C_{16}$ linear di phenyl oxide disulphonate sodium salt respectively commercially available by DOW under the trade name Dowfax 2A1® and Dowfax 8390®.

Other anionic surfactants useful herein include salts (including, for example, sodium, potassium, ammonium, and substituted ammonium salts such as mono-, di- and triethanolamine salts) of soap, $C_8$-$C_{24}$ olefinsulfonates, sulphonated polycarboxylic acids prepared by sulphonation of the pyrolyzed product of alkaline earth metal citrates, e.g., as described in British patent specification No. 1,082,179, $C_8$-$C_{24}$ alkylpolyglycolethersulfates (containing up to 10 moles of ethylene oxide); alkyl ester sulfonates such as $C_{14}$-$C_{16}$ methyl ester sulfonates; acyl glycerol sulfonates, fatty oleyl glycerol sulfates, alkyl phenol ethylene oxide ether sulfates, alkyl phosphates, isethionates such as the acyl isethionates, N-acyl taurates, alkyl succinamates and sulfosuccinates, monoesters of sulfosuccinate (especially saturated and unsaturated $C_{12}$-$C_{18}$ monoesters) diesters of sulfosuccinate (especially saturated and unsaturated $C_6$-$C_{14}$ diesters), acyl sarcosinates, sulfates of alkylpolysaccharides such as the sulfates of alkylpolyglucoside (the nonionic nonsulfated compounds being described below), alkyl polyethoxy carboxylates such as those of the formula $RO(CH_2CH_2O)_kCH_2COO^-M^+$ wherein R is a $C_8$-$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23.

Zwitterionic surfactants represent another class of preferred surfactants within the context of the present invention.

Zwitterionic surfactants contain both cationic and anionic groups on the same molecule over a wide pH range. The typical cationic group is a quaternary ammonium group, although other positively charged groups like sulfonium and phosphonium groups can also be used. The typical anionic groups are carboxylates and sulfonates, preferably sulfonates, although other groups like sulfates, phosphates and the like, can be used. Some common examples of these detergents are described in the patent literature: U.S. Pat. Nos. 2,082,275, 2,702,279 and 2,255,082.

A specific example of a zwitterionic surfactant is 3-(N-dodecyl-N,N-dimethyl)-2-hydroxypropane-1-sulfonate (Lauryl hydroxyl sultaine) available from the McIntyre Company (24601 Governors Highway, University Park, Ill. 60466, USA) under the tradename Mackam LHS®. Another specific zwitterionic surfactant is $C_{12-14}$ acylamidopropylene (hydroxypropylene) sulfobetaine that is available from McIntyre under the tradename Mackam 50-SB®. Other very useful zwitterionic surfactants include hydrocarbyl, e.g., fatty alkylene betaines. A highly preferred zwitterionic surfactant is Empigen BB®, a coco dimethyl betaine produced by Albright & Wilson. Another equally preferred zwitterionic surfactant is Mackam 35HP®, a coco amido propyl betaine produced by McIntyre.

Another class of preferred surfactants comprises the group consisting of amphoteric surfactants. One suitable amphoteric surfactant is a $C_8$-$C_{16}$ amido alkylene glycinate surfactant ('ampho glycinate'). Another suitable amphoteric surfactant is a $C_8$-$C_{16}$ amido alkylene propionate surfactant ('ampho propionate'). Other suitable, amphoteric surfactants are represented by surfactants such as dodecylbetaalanine, N-alkyltaurines such as the one prepared by reacting dodecylamine with sodium isethionate according to the teaching of U.S. Pat. No. 2,658,072, N-higher alkylaspartic acids such as those produced according to the teaching of U.S. Pat. No. 2,438,091, and the products sold under the trade name "Miranol®", and described in U.S. Pat. No. 2,528,378.

Chelating Agents

One class of optional compounds for use herein includes chelating agents or mixtures thereof. Chelating agents can be incorporated in the compositions herein in amounts ranging from 0.0% to 10.0% by weight of the total composition, preferably 0.01% to 5.0%.

Suitable phosphonate chelating agents for use herein may include alkali metal ethane 1-hydroxy diphosphonates (HEDP), alkylene poly (alkylene phosphonate), as well as amino phosphonate compounds, including amino aminotri (methylene phosphonic acid) (ATMP), nitrilo trimethylene phosphonates (NTP), ethylene diamine tetra methylene phosphonates, and diethylene triamine penta methylene phosphonates (DTPMP). The phosphonate compounds may be present either in their acid form or as salts of different cations on some or all of their acid functionalities. Preferred phosphonate chelating agents to be used herein are diethylene triamine penta methylene phosphonate (DTPMP) and ethane 1-hydroxy diphosphonate (HEDP). Such phosphonate chelating agents are commercially available from Monsanto under the trade name DEQUEST®.

Polyfunctionally-substituted aromatic chelating agents may also be useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelating agent for use herein is ethylene diamine N,N'-disuccinic acid, or alkali metal, or alkaline earth, ammonium or substitutes ammonium salts thereof or mixtures thereof. Ethylenediamine N,N'-disuccinic acids, especially the (S,S) isomer have been extensively described in U.S. Pat. No. 4,704,233, Nov. 3, 1987, to Hartman and Perkins. Ethylenediamine N,N'-disuccinic acids is, for instance, commercially available under the tradename ssEDDS® from Palmer Research Laboratories.

Suitable amino carboxylates for use herein include ethylene diamine tetra acetates, diethylene triamine pentaacetates, diethylene triamine pentaacetate (DTPA), N-hydroxyethylethylenediamine triacetates, nitrilotri-acetates, ethylenediamine tetrapropionates, triethylenetetraaminehexa-acetates, ethanol-diglycines, propylene diamine tetracetic acid (PDTA) and methyl glycine di-acetic acid (MGDA), both in their acid form, or in their alkali metal, ammonium, and substituted ammonium salt forms. Particularly suitable amino carboxylates to be used herein are diethylene triamine penta acetic acid, propylene diamine tetracetic acid (PDTA) which is, for instance, commercially available from BASF under the trade name Trilon FS® and methyl glycine di-acetic acid (MGDA).

Further carboxylate chelating agents for use herein include salicylic acid, aspartic acid, glutamic acid, glycine, malonic acid or mixtures thereof.

Radical Scavenger

The compositions of the present invention may further comprise a radical scavenger or a mixture thereof.

Suitable radical scavengers for use herein include the well-known substituted mono and dihydroxy benzenes and their analogs, alkyl and aryl carboxylates and mixtures thereof. Preferred such radical scavengers for use herein include di-tert-butyl hydroxy toluene (BHT), hydroquinone, di-tert-butyl hydroquinone, mono-tert-butyl hydroquinone, tert-butyl-hydroxy anysole, benzoic acid, toluic acid, catechol, t-butyl catechol, benzylamine, 1,1,3-tris(2-methyl-4-hydroxy-5-t-butylphenyl) butane, n-propyl-gallate or mixtures thereof and highly preferred is di-tert-butyl hydroxy toluene. Such radical scavengers like N-propyl-gallate may be commercially available from Nipa Laboratories under the trade name Nipanox S1®.

Radical scavengers, when used, may be typically present herein in amounts up to 10% by weight of the total composition and preferably from 0.001% to 0.5%. The presence of radical scavengers may contribute to the chemical stability of the compositions of the present invention.

Perfume

Suitable perfume compounds and compositions for use herein are for example those described in EP-A-0 957 156 under the paragraph entitled "Perfume", on page 13. The compositions herein may comprise a perfume ingredient, or mixtures thereof, in amounts up to 5.0% by weight of the total composition, preferably in amounts of 0.1% to 1.5%.

Dye

The liquid compositions according to the present invention may be coloured. Accordingly, they may comprise a dye or a mixture thereof.

Delivery Form of the Compositions

The compositions herein may be packaged in a variety of suitable packaging known to those skilled in the art, such as plastic bottles for pouring liquid compositions, squeeze bottles or bottles equipped with a trigger sprayer for spraying liquid compositions. Alternatively, the paste-like compositions according to the present invention may by packaged in a tube.

In an alternative embodiment herein, a kit is provided comprising the liquid composition herein and a substrate, preferably said substrate is impregnated with said composition, preferably the substrate is in the form of a flexible, thin sheet or a block of material, such as a sponge.

Suitable substrates are woven or non-woven sheets, cellulosic material based sheets, sponge or foam with open cell structures e.g.: polyurethane foams, cellulosic foam, melamine foam, etc.

Alternatively, the substrate may comprise, or be coated with, the abrasive particles described herein in absence or in combination with a liquid cleaning composition.

The Process of Cleaning a Surface

The present invention encompasses a process of cleaning and/or cleansing a surface with a liquid composition according to the present invention. Suitable surfaces herein are described herein above under the heading "The liquid cleaning/cleansing composition".

In a preferred embodiment said surface is contacted with the composition according to the present invention, preferably wherein said composition is applied onto said surface.

In another preferred embodiment, the process herein comprises the steps of dispensing (e.g., by spraying, pouring, squeezing) the liquid composition according to the present invention from a container containing said liquid composition and thereafter cleaning and/or cleansing said surface.

The composition herein may be in its neat form or in its diluted form.

By "in its neat form", it is to be understood that said liquid composition is applied directly onto the surface to be treated without undergoing any dilution, i.e., the liquid composition herein is applied onto the surface as described herein.

By "diluted form", it is meant herein that said liquid composition is diluted by the user typically with water. The liquid composition is diluted prior to use to a typical dilution level of up to 10 times its weight of water. A usually recommended dilution level is a 10% dilution of the composition in water.

The composition herein may be applied using an appropriate implement, such as a mop, paper towel, brush (e.g., a toothbrush) or a cloth, or applied directly by hand, soaked in the diluted or neat composition herein. Furthermore, once applied onto said surface said composition may be agitated over said surface using an appropriate implement. Indeed, said surface may be wiped using a mop, paper towel, brush or a cloth.

The process herein may additionally contain a rinsing step, preferably after the application of said composition. By "rinsing", it is meant herein contacting the surface cleaned/cleansed with the process according to the present invention with substantial quantities of appropriate solvent, typically water, directly after the step of applying the liquid composition herein onto said surface. By "substantial quantities", it is meant herein between 0.01 lt. and 1 lt. of water per m$^2$ of surface, more preferably between 0.1 lt. and 1 lt. of water per m$^2$ of surface.

In a preferred embodiment herein, process of cleaning is a process of cleaning household hard surfaces with a liquid composition according to present invention.

The Process for Generating Shaped Particles

A process for generating shaped non-spherical and/or non-rolling abrasive cleaning particles for use in a liquid cleaning and/or cleansing composition, may comprise the steps of:
  i. extruding a material, preferably a thermoplastic or mineral material (preferably a curable mineral comprising slurry), through an extruder nozzle orifice along an extruding axis, preferably wherein the temperature at said nozzle is kept at a temperature Tn, wherein Tn=Tm−T, and T is greater than 20° C., preferably from 30° C. to 180° C., more preferably from 50° C. to 150° C., Tm being the melting temperature of said thermoplastic material;
  ii. slicing the extruded thermoplastic material into extruded elements having a predetermined length, preferably length "L"; and
  iii. optionally adding said extruded elements to a composition, preferably a liquid detergent composition or impregnated substrate,
wherein the extruder nozzle orifice has a predetermined shape and comprises a complex cross-sectional shape on a plane perpendicular to said extruding axis, said complex cross-sectional shape being the inverse image of the complex cross-sectional shape of the extruded elements herein.

In a preferred embodiment the extruded elements are cooled immediately after exiting the extruder nozzle such that the temperature of the outer surfaces of the extruded element drops by at least 30%, preferably at least 40%, preferably at least 50%, more preferably at least 60%, most preferably at least 70%, in the first 10 seconds of exit. Such cooling may be achieved by directly contacting the element with a coolant such as water or by cooling the extrusion area outside the extruder nozzle.

An alternative process comprises the steps of providing a CAD (Computer Aided Design) file comprising a 3D (three dimensional) virtual design of the element to be generated as single abrasive cleaning particle described herein, inputting said CAD file to a 3D printer for the 3D printer to generate a physical copy of said virtual design, preferably a plurality of said physical copies, and optionally adding said physical copies to a composition, preferably a liquid detergent composition or impregnated substrate.

Method to Determine the Orientation of the Particle During the Cleaning Event

A sufficient amount of particles is poured randomly on the surface of a glass tile. By sufficient amount of particles, it is understood that the particle number at the surface of the tile will be high enough to allow analysis of at least 50 particles, preferably more than 100 and low enough in order that the particles are separated from one another in order to not compromise the natural orientation of each particle individually from one another during the cleaning motion, e.g. a total of about 300 particles on a 25 cm×25 cm surface.

A Spontex® cellulose sponge pre-wetted with water is then mounted on a Wet Abrasion Scrub Tester Instrument (such as made by Sheen Instruments Ltd. Kingston, England). The abrasion tester is configured to supply pressure of e.g.: 200 g, and move the sponge over the test surface with a set stroke length of e.g.: 10 cm, at set speed of e.g.: 37 strokes per minute. After 20 strokes, the experiment is stopped and the tile is subjected to microscope/image analysis, whereas the particle are observed from the opposite face of the glass tile without removing the sponge from the glass tile. The orientation angle of the element is measured as being the angle of the Z-axe of the element and the cleaning direction. The orientation angle is measured on at least 50 particles, preferably 100 or more particles

EXAMPLES

|  | Particle Example# | | | | | |
| --- | --- | --- | --- | --- | --- | --- |
|  | 1 | 2 | 3 | 4 | 5 | 6 |
| Raw material | PU | PHB | PHB | PHB | PHB | PHBV |
| Ratio L/ECD P$_{Hull}$ | 1.5 | 1 | 1.5 | 2 | 3 | 0.5 |
| Form Factor (cross-sectional shape) | 0.15 | 0.25 | 0.4 | 0.35 | 0.7 | 0.25 |
| Solidity (cross-sectional shape) | 0.65 | 0.8 | 0.35 | 0.50 | 0.75 | 0.65 |
| Aspect Ratio (cross-sectional shape) | 0.4 | 0.35 | 0.5 | 0.2 | 0.7 | 0.55 |
| Particle Area-equivalent diameter "ECD" (in μm) | 250 | 250 | 150 | 200 | 100 | 350 |

|  | Particle Example cntd. # | | | | | |
| --- | --- | --- | --- | --- | --- | --- |
|  | 7 | 8 | 9 | 10 | 11 | 12 |
| Raw material | PHBV | PHBV | PHBV | PHBV | PLA | PLA |
| Ratio L/ECD P$_{Hull}$ | 1 | 1.5 | 2 | 2.5 | 0.8 | 1.5 |

-continued

| | | | | | | |
|---|---|---|---|---|---|---|
| Form Factor (cross-sectional shape) | 0.35 | 0.4 | 0.4 | 0.4 | 0.15 | 0.5 |
| Solidity (cross-sectional shape) | 0.70 | 0.55 | 0.25 | 0.50 | 0.65 | 0.70 |
| Aspect Ratio (cross-sectional shape) | 0.5 | 0.3 | 0.6 | 0.4 | 0.4 | 0.2 |
| Particle Area-equivalent diameter "ECD" (in μm) | 100 | 200 | 250 | 250 | 300 | 400 |

| | Particle Example cntd. # | | | | | |
|---|---|---|---|---|---|---|
| | 13 | 14 | 15 | 16 | 17 | 18 |
| Raw material | PLA | PCL | PCL | PBS | PBAT | PBAT |
| Ratio L/ECD $P_{Hull}$ | 2 | 1 | 1.7 | 0.5 | 1 | 1.5 |
| Form Factor (cross-sectional shape) | 0.35 | 0.2 | 0.35 | 0.35 | 0.35 | 0.45 |
| Solidity (cross-sectional shape) | 0.55 | 0.65 | 0.50 | 0.50 | 0.35 | 0.35 |
| Aspect Ratio (cross-sectional shape) | 0.6 | 0.33 | 0.4 | 0.5 | 0.33 | 0.5 |
| Particle Area-equivalent diameter "ECD" (in μm) | 125 | 400 | 250 | 300 | 250 | 200 |

| | Particle Example cntd. # | | | | | |
|---|---|---|---|---|---|---|
| | 19 | 20 | 21 | 22 | 23 | 24 |
| Raw material | PBAT | TPS | KAO | CAC | BAS | MICA |
| Ratio L/ECD $P_{Hull}$ | 2 | 1.5 | 2 | 2 | 1.5 | 1.5 |
| Form Factor (cross-sectional shape) | 0.5 | 0.3 | 0.4 | 0.35 | 0.25 | 0.6 |
| Solidity (cross-sectional shape) | 0.8 | 0.55 | 0.6 | 0.5 | 0.65 | 0.6 |
| Aspect Ratio (cross-sectional shape) | 0.7 | 0.7 | 0.7 | 0.6 | 0.55 | 0.4 |
| Particle Area-equivalent diameter "ECD" (in μm) | 300 | 200 | 25 | 20 | 15 | 20 |

| | Particle Example cntd. # | | | | | |
|---|---|---|---|---|---|---|
| | 25 | 26 | 27 | 28 | 29 | 30 |
| Raw material | TALC | KAOb | CACb | BASb | MICAb | TALCb |
| Ratio L/ECD $P_{Hull}$ | 2.5 | 1.5 | 1.5 | 2 | 2 | 2 |
| Form Factor (cross-sectional shape) | 0.3 | 0.35 | 0.35 | 0.20 | 0.4 | 0.4 |
| Solidity (cross-sectional shape) | 0.55 | 0.5 | 0.7 | 0.25 | 0.35 | 0.5 |
| Aspect Ratio (cross-sectional shape) | 0.5 | 0.7 | 0.5 | 0.4 | 0.2 | 0.15 |
| Particle Area-equivalent diameter "ECD" (in μm) | 15 | 200 | 250 | 300 | 250 | 250 |

Symbol Foam Material:
PU=Polyurethane (CAS number 53862-89-8 or 57029-46-6)
PHB=Polyhydroxybutyrate (CAS number 26063-00-3 ex.: from Tianan or Biomer)
PHBV=Polyhydroxybutyrate-co-valerate (CAS number 80181-31-3 ex.: from Tianan or Biomer)
PLA=Polylactic acid (CAS number 26100-51-6 ex.: from NatureWorks)
PCL=Polycaprolactone (CAS number 24980-41-4 ex. from Perstorp)
PBS=Polybutylene succinate (CAS number 10034-55-6.ex.: from CSM)
PBAT=Polybutylene adipate terephtalate (CAS number 10034-55-6.ex.: from BASF)
TPS=Thermoplastic starch (CAS number 9005-25-8 e.g.: from Aldrich)
KAO=Kaolinite (CAS number 1318-74-7 from Aldrich). Note: extruded from water slurry 30-60% solid content and dry/cured after extrusion in 500-1200° C. temperature range
CAC=Calcium Carbonate (CAS number 471-34-1 from Aldrich). Note: extruded from water slurry 30-60% solid content and dry/cured after extrusion in 500-1200° C. temperature range
BAS=Barium sulfate (e.g.: CAS number 7727-43-7 from KOBO or Aldrich). Note: extruded from water slurry 30-60% solid content and dry/cured after extrusion in 500-1200° C. temperature range
MICA=Mica (e.g.: CAS number 12001-26-2 sieved or commuted from Mica Y1800, Y3000, S25 from KOBO). Note: extruded from water slurry 30-60% solid content and dry/cured after extrusion in 500-1200° C. temperature range
TALC=Talc (CAS number 14807-96-6 sieved or commuted from Kobo AJM, Ex-15, CT-250 or from Imerys OOSC, Superior M10 DEC). Note: extruded from water slurry 30-60% solid content and dry/cured after extrusion in 500-1200° C. temperature range
KAOb=Blend 50% Kaolinite (CAS number 1318-74-7 from Aldrich) and 50% Carnauba wax (CAS number 8015-86-9 from Aldrich). Note: extruded from water slurry 30-60% solid content and dry/cured after extrusion in 500-1200° C. temperature range
CACb=Blend 50% Calcium Carbonate (CAS number 471-34-1 from Aldrich) and 50% Carnauba wax (CAS number 8015-86-9 from Aldrich)
BASb=Blend 50% Barium sulfate (e.g.: CAS number 7727-43-7 from KOBO or Aldrich) and 50% Carnauba wax (CAS number 8015-86-9 from Aldrich)
MICAb=Blend 50% Mica (e.g.: CAS number 12001-26-2 sieved or commuted from Mica Y1800, Y3000, S25 from KOBO) and 50% Carnauba wax (CAS number 8015-86-9 from Aldrich)
TALCb=Blend 50% Talc (CAS number 14807-96-6 sieved or commuted from Kobo AJM, Ex-15, CT-250 or from Imerys OOSC, Superior M10 DEC) and 50% Carnauba wax (CAS number 8015-86-9 from Aldrich)

These following compositions were made comprising the listed ingredients in the listed proportions (weight %).
Examples herein are meant to exemplify the present invention but are not necessarily used to limit or otherwise define the scope of the present invention.

Examples of Abrasive-Particle Containing Formulations

Hard Surface Cleaner Bathroom Composition

| % Weight | 1 | 2 | 3 |
|---|---|---|---|
| C9-C11 EO8 (Neodol 91-8 ®) | 3 | 2.5 | 3.5 |
| Alkyl Benzene sulfonate | | 1 | |
| C12-14-dimethyl Aminoxide | | 1 | |
| n-Butoxy Propoxy Propanol | | 2 | 2.5 |
| Hydrogene Peroxide | 3 | | |
| Hydrophobic ethoxylated polyurethane (Acusol 882 ®) | 1.5 | 1 | 0.8 |
| Lactic Acid | 3 | | 3.5 |
| Citric Acid | | 3 | 0.5 |
| Polysaccharide (Xanthan Gum, Keltrol CG-SFT ® Kelco) | 0.25 | 0.25 | 0.25 |
| Perfume | 0.35 | 0.35 | 0.35 |
| .Abrasive cleaning particle example # | 1 | 2 | 6 |
| .Abrasive cleaning particle load | 1 | 1 | 1 |
| Water | Balance | Balance | Balance |

Hard Surface Cleaner Bathroom Composition (Cont.):

| % Weight | 4 | 5 | 6 |
|---|---|---|---|
| Chloridric acid | 2 | | |
| Linear C10 alkyl sulphate | 1.3 | 2 | 3 |
| n-Butoxy Propoxy Propanol | 2 | | 1.75 |
| Citric Acid | | 3 | 3 |
| PolyvinylPyrrolidone (Luviskol K60 ®) | 0.1 | 0.1 | 0.1 |
| NaOH | | 0.2 | 0.2 |
| Perfume | 0.4 | 0.4 | 0.4 |
| Polysaccharide (Xanthan Gum Kelzan T ®, Kelco) | 0.3 | 0.35 | 0.35 |
| .Abrasive cleaning particle example # | 9 | 10 | 11 |
| .Abrasive cleaning particle load | 2 | 2 | 2 |
| Water | Balance | Balance | Balance |

Hand-Dishwashing Detergent Compositions:

| % Weight | 7 | 8 | 9 |
|---|---|---|---|
| N-2-ethylhexyl sulfocuccinamate | 3 | 3 | 3 |
| C11EO5 | 7 | 14 | |
| C11-EO7 | | | 7 |
| C10-EO7 | 7 | | 7 |
| Trisodium Citrate | 1 | 1 | 1 |
| Potassium Carbonate | 0.2 | 0.2 | 0.2 |
| Perfume | 1 | 1 | 1 |
| Polysaccharide (Xanthan Gum Kelzan T ®, Kelco) | 0.35 | 0.35 | 0.35 |
| .Abrasive cleaning particle example # | 1 | 6 | 9 |
| .Abrasive cleaning particle load | 1 | 2 | 5 |
| Water (+minor e.g.; pH adjusted to 10.5) | Balance | Balance | Balance |

General Degreaser Composition:

| % Weight | 10 | 11 |
|---|---|---|
| C9-C11 EO8 (Neodol 91-8 ®) | 3 | 3 |
| N-Butoxy Propoxy Propanol | 15 | 15 |
| Ethanol | 10 | 5 |
| Isopropanol | | 10 |
| Polysaccharide (Xanthan Gum-glyoxal modified Optixan-T) | 0.35 | 0.35 |
| .Abrasive cleaning particle example # | 15 | 19 |
| .Abrasive cleaning particle load | 2 | 3 |
| Water (+minor e.g.; pH adjusted to alkaline pH) | Balance | Balance |

Scouring Composition:

| % Weight | 12 | 13 | 14 |
|---|---|---|---|
| Sodium C13-16 prafin sulfonate | 2.5 | 2.5 | 2.5 |
| C12-14-EO7 (Lutensol AO7 ®) | 0.5 | 0.5 | 0.5 |
| Coconut Fatty Acid | 0.3 | 0.3 | 0.3 |
| Sodium Citrate | 3.3 | 3.3 | 3.3 |
| Sodium Carbonate | 3 | 3 | 3 |
| Orange terpenes | 2.1 | 2.1 | 2.1 |
| Benzyl Alcohol | 1.5 | 1.5 | |
| Polyacrylic acid 1.5 Mw | 0.75 | 0.75 | 0.75 |
| .Abrasive cleaning particle example # | 26 | 27 | 6 |
| .Abrasive cleaning particle load | 10 | 10 | 10 |
| Water | Balance | Balance | Balance |

Liquid Glass Cleaner:

| % Weight | 15 | 16 |
|---|---|---|
| Butoxypropanol | 2 | 4 |
| Ethanol | 3 | 6 |
| C12-14 sodium sulphate | 0.24 | |
| NaOH/Citric acid | To pH 10 | |
| Citric Acid | | |
| .Abrasive cleaning particle example # | 5 | 5 |
| .Abrasive cleaning particle load | 0.5 | 0.5 |
| Water (+minor) | Balance | Balance |

Cleaning Wipe (Body Cleansing Wipe):

| % Weight | 17 | 18 | 19 |
|---|---|---|---|
| C10 Amine Oxide | — | 0.02 | — |
| C12,14 Amine Oxide | 0.4 | — | — |
| Betaine (Rewoteric AM CAS 15 U) | — | — | 0.2 |
| C9,11 A5EO (Neodol E 91.5 ®) | — | 0.1 | — |
| C9,11 A8EO (Neodol E 91.8 ®) | — | — | 0.8 |
| C12,14 A5EO | 0.125 | — | — |
| 2-Ethyl Hexyl Sulphate | — | 0.05 | 0.6 |
| Silicone | 0.001 | 0.003 | 0.003 |
| EtOH | 9.4 | 8.0 | 9.5 |
| Propylene Glycol Butyl Ether | 0.55 | 1.2 | — |
| Geraniol | — | — | 0.1 |
| Citric acid | 1.5 | — | — |
| Lactic acid | — | — | 1.5 |
| Perfume | 0.25 | 0.15 | 0.15 |
| Abrasive cleaning particle example # | 13 | 3 | 7 |
| Abrasive cleaning particle load | 0.5 gram/m$^2$ | 1 gram/m$^2$ | 3 gram/m$^2$ |
| Nonwoven: Spunlace 100% viscose 50 gsm (lotion loading fact) | | | (x3.5) |
| Nonwoven: Airlaid walkisoft (70% cellulose, 12% Viscose, 18% binder) 80 gsm (lotion loading factor) | | (x3.5) | |
| Carded thermobonded (70% polypropylene, 30% rayon), 70 gsm (Lotion loading factor) | (x3.5) | | |

Cleaning Wipe (Body Cleansing Wipe):

| % Weight | 20 |
|---|---|
| Benzalkonioum Chloride (Alkaquat DMB-451 ®) | 0.1 |
| Cocamine Oxide (C10/C16 alkyl dimethyl amine oxide) AO-1214 LP supplied by Procter & Gamble Co.) | 0.5 |
| Pyroglutamic Acid (pidolidone) (2-pyrrolidone-5 carboxylic acid) | 4 |
| Ethanol-denatured 200 proof (SD alcohol 40 ®) | 10 |
| DC Antiform H-10 (dimethicone) | 0.03 |

-continued

| % Weight | 20 |
|---|---|
| Sodium Benzoate | 0.2 |
| Tetrasodium EDTA (Hampene 220 ®) | 0.1 |
| Sodium Chloride | 0.4 |
| Perfume | 0.01 |
| Abrasive cleaning particle example # | 5 |
| Abrasive cleaning particle load | 2 gram/m$^2$ |
| Water and minors | balance |

The above wipes lotion composition is loaded onto a water-insoluble substrate, being a patterned hydroentangled non-woven substrate having a basis weight of 56 grams per square meter comprising 70% polyester and 30% rayon approximately 6.5 inches wide by 7.5 inches long with a caliper of about 0.80 mm. Optionally, the substrate can be pre-coated with dimethicone (Dow Corning 200 Fluid 5 cst) using conventional substrate coating techniques. Lotion to wipe weight ratio of about 2:1 using conventional substrate coating techniques.

Body Cleansing Composition:

| % Weight | 21 | 22 |
|---|---|---|
| Cocoamidopropyl betaine | 5.15 | 5.15 |
| Sodium Laureth sulfate | 5.8 | 5.8 |
| Sodium Lauroyl sarcosinate | 0.5 | 0.5 |
| Polyquaternium 10 | 0.1 | 0.1 |
| C12-14 fatty alcohol | 0.45 | 0.45 |
| Zinc Stearate | 1.5 | 1.5 |
| Glycol DiStearate | 0.25 | 0.25 |
| Sodium lauryl sulfate | 0.53 | 0.53 |
| Cocoamidopropyl betaine | 0.17 | 0.17 |
| Lauramide Diethanolamide | 0.48 | 0.48 |
| Sodium sulfate | 0.05 | 0.05 |
| Citric Acid | 0.05 | 0.05 |
| DMDM hydantoin (1,3-Dimethylol-5,5-dimethylhydantoin Glydant) | 0.2 | 0.2 |
| Tetra Sodium EDTA | 0.1 | 0.1 |
| Fragance | 0.5 | 0.5 |
| Polysaccharide (Xanthan Gum-glyoxal modified Optixan-T) | 0.2 | 0.2 |
| Abrasive cleaning particle example # | 29 | 30 |
| Abrasive cleaning particle load | 2 | 2 |
| Water and minors | | 1 |
| Water | Balance | Balance |

Hair Shampoo

| | 23 | 24 | 25 |
|---|---|---|---|
| Water | q.s. | q.s. | q.s. |
| Polyquaterium 76 [1] | 0.25 | — | — |
| Guar, Hydroxylpropyl Trimonium Chloride [2] | — | 0.25 | — |
| Polyquaterium 6 [3] | — | — | 0.25 |
| Sodium Laureth Sulfate | 12 | 10.5 | 10.5 |
| Sodium Lauryl Sulfate | | 1.5 | 1.5 |
| Silicone [4] | 0.75 | 1.00 | 0.5 |
| Cocoamidopropyl Betaine | 3.33 | 3.33 | 3.33 |
| Cocoamide MEA | 1.0 | 1.0 | 1.0 |
| Ethylene Glycol Distearate | 1.50 | 1.50 | 1.50 |
| Abrasive cleaning particle example # | 1 | 6 | 14 |
| Abrasive cleaning particle load | 1 | 2 | 3 |
| Fragrance | 0.70 | 0.70 | 0.70 |
| Preservatives, pH & Visc. adjusters | Up to 1% | Up to 1% | Up to 1% |

[1] Copolymer of Acrylamide(AM) and TRIQUAT, MW = 1,000,000; CD = 1.6 meq./gram; Rhodia
[2] Jaguar C500, MW - 500,000, CD = 0.7, Rhodia
[3] Mirapol 100S, 31.5% active, Rhodia
[4] Dimethicone Fluid, Viscasil 330M; 30 micron particle size; Momentive Silicones Facial Cleansing Compositions

| Ingredients | 26 | 27 | 28 | 29 |
|---|---|---|---|---|
| Acrylates Copolymer[1] | 1.50 | 2.0 | 1.25 | — |
| Acrylates/C$_{10-30}$ alkyl acrylate crosspolymer[2] | — | — | — | 1.0 |
| Sodium Lauryl Sulfate | 2.0 | — | — | — |
| Sodium Laureth Sulfate | 8.0 | — | — | — |
| Ammonium Lauryl Sulfate | — | 6.0 | — | — |
| Sodium Trideceth Sulfate | — | — | 3.0 | 2.5 |
| Sodium Myristoyl Sarcosinate | — | 2.0 | 3.0 | 2.5 |
| Sodium Lauroamphoacetate[3] | — | — | 6.0 | 5.0 |
| Sodium Hydroxide* | pH >6 | — | — | — |
| Triethanolamine* | — | pH >6 | — | pH 5.2 |
| Cocamidopropyl Betaine | 4.0 | 7.0 | — | — |
| Glycerin | 4.0 | 5.0 | 2.0 | 2.0 |
| Sorbitol | — | — | 2.0 | 2.0 |
| Salicylic Acid | — | — | 2.0 | 2.0 |
| Fragrance | 0.1 | 0.1 | 0.1 | 0.1 |
| Preservative | 0.3 | 0.3 | 0.15 | 0.15 |
| Abrasive cleaning particle example # | 2 | 6 | 8 | 15 |
| Abrasive cleaning particle load | 1 | 1 | 2 | 2 |
| PEG 120 Methyl Glucose Trioleate[4] | 0.5 | — | 0.25 | 0.25 |
| PEG 150 Pentaerythrityl Tetrastearate[5] | — | 0.40 | — | — |
| Citric Acid** | pH 5.5 | pH 5.5 | pH 5.5 | pH 5.5 |
| Water | QS to 100% | QS to 100% | QS to 100% | QS to 100% |

*per the supplier use directions, the base is used to activate the acrylates copolymer
**acid can be added to adjust the formula to a lower pH
[1] Carbopol Aqua SF-1 ® from Noveon ™, Inc.
[2] Carbopol Ultrez 21 ® from Noveon ™, Inc.
[3] Miranol ® Ultra L32 from Rhodia
[4] Glucamate LT ® from Chemron
[5] Crothix ® from Croda Examples 24 to 27 are Made the Following Way Add Carbopol to de-ionized free water of the formulation. Add all surfactants except cationics and betaines. If the pH is less than 6 then add a neutralizing agent (typically a base i.e., Triethanolamine, sodium hydroxide) to adjust to a pH greater than 6. If necessary, apply gentle heat to reduce viscosity and help minimize air entrapment. Add betaine and/or cationic surfactants. Add conditioning agents, additional rheology modifiers, pearlizing agents, encapsulated materials, exfoliants, preservatives, dyes, fragrances, abrasive particles and other desirable ingredients. Lastly, if desired reduce the pH with an acid (i.e. citric acid) and increase viscosity by adding sodium chloride.

Oral Care Composition (Toothpaste)

| | 30 | 31 | 32 | 33 | 34 |
|---|---|---|---|---|---|
| Sodium Gluconate | 1.064 | 1.064 | 1.064 | 1.064 | 0.600 |
| Stannous fluoride | 0.454 | 0.454 | 0.454 | 0.454 | 0.454 |
| Sodium fluoride | | | | | |
| Sodium monofluorophosphate | | | | | |
| Zinc Lactate | 0.670 | 0.670 | 0.670 | 0.670 | 2.500 |
| Glycerin | — | — | — | — | 36.000 |
| Polyethylene glycol 300 | | | | | 7.000 |
| Propylene Glycol | | | | | 7.000 |
| Sorbitol(LRS) USP | 39.612 | 39.612 | 39.612 | 39.612 | — |
| Sodium lauryl sulfate solution (28%) | 5.000 | 5.000 | 5.000 | 5.000 | 3.500 |
| Abrasive cleaning particle example # | 22 | 23 | 21 | 22 | 25 |

| | 30 | 31 | 32 | 33 | 34 |
|---|---|---|---|---|---|
| Abrasive cleaning particle load | 10.000 | 10.000 | 1.000 | 5.000 | 5.000 |
| Zeodent 119 | — | — | — | — | — |
| Zeodent 109 | — | — | 10.000 | 10.000 | 10.000 |
| Hydrogen peroxide (35% soln) | — | — | — | — | — |
| Sodium hexametaphosphate | — | — | — | — | 13.000 |
| Gantrez | — | 2.000 | 2.000 | 2.000 | — |
| Natural CaCO3-600M | — | — | — | — | — |
| Sodium phosphate (mono basic) | — | — | — | — | — |
| Sodium phosphate (Tri basic) | — | — | — | — | 1.000 |
| Zeodent 165 | — | — | — | — | — |
| Cocoamidopropyl Betaine (30% Soln) | — | — | — | — | — |
| Cetyl Alcohol | 3.000 | — | — | — | — |
| Stearyl Alcohol | 3.000 | — | — | — | — |
| Hydroxyethyl cellulose (HEC Natrasol 250M) | — | 0.500 | 0.500 | 0.500 | — |
| CMC 7M8SF | — | 1.300 | 1.300 | 1.300 | — |
| Xanthan Gum | — | — | — | — | 0.250 |
| Poloxamer 407 | — | — | — | — | — |
| Carrageenan mixture | — | 0.700 | 0.700 | 0.700 | 0.600 |
| Titanium dioxide | — | — | — | — | — |
| Saccharin Sodium | 0.500 | 0.500 | 0.500 | 0.500 | 0.500 |
| Flavor | 1.000 | 1.000 | 1.000 | 1.000 | 1.000 |
| Water | QS | QS | QS | QS | QS |

Zeodent 119, 109 and 165 are precipitated silica materials sold by the J. M. Huber Corporation.
Gantrez is a copolymer of maleic anhydride or acid and methyl vinyl ether.
CMC 7M8SF is a sodium carboxymethylcellulose.
Poloxamer is a difunctional block-polymer terminating in primary hydroxyl groups.

| | 35 | 36 | 37 | 38 | 39 |
|---|---|---|---|---|---|
| Sodium Gluconate | — | — | — | — | — |
| Stannous fluoride | — | — | — | — | — |
| Sodium fluoride | — | 0.243 | 0.243 | 0.243 | — |
| Sodium monofluorophosphate | 1.10 | — | — | — | — |
| Zinc Lactate | — | — | — | — | — |
| Glycerin | — | — | — | — | 40.000 |
| Polyethylene glycol 300 | — | — | — | — | — |
| Propylene Glycol | | | | | |
| Sorbitol(LRS) USP | 24.000 | 42.500 | 42.500 | 42.500 | 30.000 |
| Sodium lauryl sulfate solution (28%) | 4.000 | 4.000 | — | 4.000 | — |
| Abrasive cleaning particle Examples # | 21 | 21 | 22 | 22 | 22 |
| Abrasive cleaning particle load | 5.000 | 10.000 | 10.000 | 5.000 | 15.000 |
| Zeodent 119 | — | — | — | 10.000 | — |
| Zeodent 109 | — | — | — | — | — |
| Hydrogen peroxide (35% soln) | — | — | — | — | — |
| Sodium hexametaphosphate | — | — | — | — | — |
| Gantrez | — | — | — | — | — |
| Natural CaCO3-600M | 35.00 | — | — | — | — |
| Sodium phosphate (mono basic) | 0.10 | 0.420 | 0.420 | 0.420 | 0.420 |
| Sodium phosphate (Tri basic) | 0.40 | 1.100 | 1.100 | 1.100 | 1.100 |
| Zeodent 165 | 2.00 | — | — | — | 2.000 |
| Cocoamidopropyl Betaine (30% Soln) | — | — | 5.000 | — | — |
| Cetyl Alcohol | 0.000 | — | — | — | — |
| Stearyl Alcohol | 0.000 | — | — | — | — |
| Hydroxyethyl cellulose (HEC Natrasol 250M) | — | 0.500 | 0.500 | 0.500 | — |
| CMC 7M8SF | 1.300 | 1.300 | 1.300 | 1.300 | 1.300 |
| Xanthan Gum | — | — | — | — | — |
| Poloxamer 407 | — | — | — | — | — |
| Carrageenan mixture | — | 0.700 | 0.700 | 0.700 | — |
| Titanium dioxide | — | — | — | — | — |
| Saccharin Sodium | 0.250 | 0.500 | 0.500 | 0.500 | 0.500 |
| Flavor | 1.000 | 1.000 | 1.000 | 1.000 | 1.000 |
| Water | QS | QS | QS | QS | QS |

| | 40 | 41 | 42 |
|---|---|---|---|
| Sodium Gluconate | — | — | 1.500 |
| Stannous fluoride | — | — | 0.454 |
| Sodium fluoride | — | — | — |
| Sodium monofluorophosphate | — | — | — |
| Zinc Lactate | — | — | — |
| Glycerin | 40.000 | 10.000 | 25.000 |
| Polyethylene glycol 300 | 3.000 | — | — |
| Propylene Glycol | — | — | — |
| Sorbitol(LRS) USP | — | 39.612 | — |
| Sodium lauryl sulfate solution (28%) | 5.000 | 4.000 | 4.000 |
| Abrasive cleaning particle Examples # | 23 | 25 | 25 |
| Abrasive cleaning particle load | 15.000 | 5.000 | 5.000 |
| Zeodent 119 | — | — | — |
| Zeodent 109 | — | — | — |
| Hydrogen peroxide (35% soln) | — | 8.570 | 8.570 |
| Sodium hexametaphosphate | 14.000 | — | — |
| Gantrez | — | — | — |
| Natural CaCO3-600M | — | — | — |
| Sodium phosphate (mono basic) | 0.420 | — | — |
| Sodium phosphate (Tri basic) | 1.100 | — | — |
| Zeodent 165 | 2.000 | — | — |
| Cocoamidopropyl Betaine (30% Soln) | — | — | — |
| Cetyl Alcohol | — | 3.000 | — |
| Stearyl Alcohol | — | 3.000 | — |
| Hydroxyethyl cellulose (HEC Natrasol 250M) | — | — | — |
| CMC 7M8SF | 1.000 | — | — |
| Xanthan Gum | 0.300 | — | — |
| Poloxamer 407 | 0.500 | — | 18.000 |
| Carrageenan mixture | — | — | — |
| Titanium dioxide | 0.500 | — | — |
| Saccharin Sodium | 0.500 | 0.500 | 0.500 |
| Flavor | 1.000 | 1.000 | 1.000 |
| Water | QS | QS | QS |

Oral Care Composition (Toothpaste):

| % Weight | 43 | 44 |
|---|---|---|
| Sorbitol (70% sol.) | 24.2 | 24.2 |
| Glycerin | 7 | 7 |
| Carboxymethylcellulose | 0.5 | 0.5 |
| PEG-6 | 4 | 4 |
| Sodium Fluoride | 0.24 | 0.24 |
| Sodium Saccharine | 0.13 | 0.13 |
| Mono Sodium phosphate | 0.41 | 0.41 |
| Tri Sodium phosphate | 0.39 | 0.39 |
| Sodium Tartrate | 1 | 1 |
| TiO2 | 0.5 | 0.5 |
| Silica | 35 | |
| Sodium lauroyl sarcosinate (95% active) | 1 | 1 |
| Flavor | 0.8 | 0.8 |
| Abrasive cleaning particle example # | 21 | 22 |
| Abrasive cleaning particle load | 12 | 10 |
| Water | Balance | Balance |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid cleaning and/or cleansing composition comprising non-spherical and/or non-rolling abrasive cleaning particles characterized in that said abrasive cleaning particles comprise extruded, and/or three-dimensional printed, elements having a longitudinal length extending parallel to a z-axis and a complex cross-sectional shape extending on a plane perpendicular to said longitudinal length and parallel to an x-y plane, wherein said complex cross-sectional shape comprises one or more elongate protrusions projecting in a direction parallel to the longitudinal length, each protrusion having at least one edge, and wherein said complex cross-sectional shape is a non-random cross-sectional shape, and wherein said elements comprise a hollow core and are porous, wherein said elements comprise within said hollow core and/or pores an active component selected from the group consisting of cleaning actives, solvent, polymer acid, polymer base, malodor counteractant, perfume, and mixtures thereof.

2. A liquid cleaning and/or cleansing composition according to claim 1 wherein the abrasive cleaning particles consist of said elements.

3. A liquid cleaning and/or cleansing composition according to claim 1 wherein the protrusions project along substantially the entire length.

4. A liquid cleaning and/or cleansing composition according to claim 1 wherein said elements are symmetrical or asymmetrical about a plane parallel to said longitudinal length.

5. A liquid cleaning and/or cleansing composition according to claim 1 wherein said elements consist of a single continuous fiber of organic or inorganic material.

6. A liquid cleaning and/or cleansing composition according to claim 1 wherein said complex cross-sectional shape comprises more than about 2 elongate protrusions in the form of abrasive wings having a shape selected from the group consisting of substantially linear, substantially concave, substantially convex and combinations thereof.

7. A liquid cleaning and/or cleansing composition according to claim 1 wherein said complex cross-sectional shape comprises from about 3 to about 30 of said protrusions, in the form of abrasive wings having a shape selected from the group consisting of substantially linear, substantially concave, substantially convex and combinations thereof.

8. A liquid cleaning and/or cleansing composition according to claim 1 wherein the complex cross-sectional shape has an aspect ratio $F_{min}/F_{max}$ of less than 1.

9. A liquid cleaning and/or cleansing composition according to claim 1 wherein said edge exhibits an angle of from about 10° to about 90°.

10. A liquid cleaning and/or cleansing composition according to claim 1 wherein each said protrusion has at least one edge having a tip diameter of from greater than about 1 µm to less than about 50 µm.

11. A liquid cleaning and/or cleansing composition according to claim 1 wherein said abrasive cleaning particles have a packing density of from about 50 kg/m³ to about 400 kg/m³.

12. A liquid cleaning and/or cleansing composition according to claim 1 wherein more than about 70% of the particle population exhibit the same shape.

13. A liquid cleaning and/or cleansing composition according to claim 1 wherein the abrasive particles comprise a material selected from the group consisting of polyethylene, polypropylene, polyvinyl chloride, polycarbonate, melamine, urea, polyurethane, polyacrylate, polystyrene, phenolic polyesters, polyamide, minerals, and mixtures thereof.

14. A liquid cleaning and/or cleansing composition according to claim 1 wherein the abrasive particles comprise a biodegradable material having a biodegradability rate of greater than about 50% according to ASTM6400 test method.

15. A liquid cleaning and/or cleansing composition according to claim 1 wherein the abrasive particles comprise from about 5 to about 70%, by weight of particle, of reinforcing filler particles wherein said filler particles comprise a material selected from the group consisting of organic, in-organic and mixtures thereof.

16. A liquid cleaning and/or cleansing composition according to claim 1 wherein the abrasive particles have a Mohs hardness of from about 1 to about 5.5.

17. A liquid cleaning and/or cleansing composition according to claim 1 further comprising a suspending aid.

18. A kit comprising a composition according to claim 1 and a substrate selected from the group consisting of paper, nonwoven towel or wipe, sponge, and combinations thereof.

19. An impregnated or coated substrate comprising a material selected from the group consisting of paper, nonwoven towel or wipe, sponge, and combinations thereof, and a composition according to claim 1.

* * * * *